(12) United States Patent
Brechtelsbauer et al.

(10) Patent No.: US 7,199,242 B2
(45) Date of Patent: Apr. 3, 2007

(54) PROCESSES FOR THE PRODUCTION OF AMINO-PROTECTED DERIVATIVES OF 4-AMINOMETHYLENE-PYRROLIDIN-3-ONE AND/OR 4-AMINOMETHYLENE-PYRROLIDIN-3-ALKOXYIMINO DERIVATIVES AND/OR GEMIFLOXACIN OR A SALT THEREOF

(75) Inventors: Clemens Michael Helmut Brechtelsbauer, Tonbridge (GB); Stephen Thomas Carpenter, Tonbridge (GB); Trevor John Grinter, Tonbridge (GB); Michael Anthony Harris, Tonbridge (GB); Yeongdae Kim, Daejon (KR); Youngwoon Kwon, Daejon (KR); Dongchul Lee, Daejon (KR); François Xavier Ricard, Tonbridge (GB); Richard Neville Saunders, Tonbridge (GB)

(73) Assignee: LG Life Sciences Limited, Youngdunpo-Gu, Seoul (KR)

( * ) Notice: Subject to any disclaimer, the term of this patent is extended or adjusted under 35 U.S.C. 154(b) by 0 days.

(21) Appl. No.: 10/485,488

(22) PCT Filed: Aug. 2, 2002

(86) PCT No.: PCT/GB02/03585

§ 371 (c)(1),
(2), (4) Date: Jul. 27, 2004

(87) PCT Pub. No.: WO03/011450

PCT Pub. Date: Feb. 13, 2003

(65) Prior Publication Data

US 2005/0043546 A1 Feb. 24, 2005

(30) Foreign Application Priority Data

Aug. 2, 2001 (GB) .................................. 0118938.0
Jul. 30, 2002 (GB) .................................. 0217637.8

(51) Int. Cl.
*C07D 471/02* (2006.01)
*C07D 207/46* (2006.01)
(52) U.S. Cl. .................................... 546/123; 548/550
(58) Field of Classification Search ................ 546/123; 548/550
See application file for complete search history.

(56) References Cited

U.S. PATENT DOCUMENTS

| 5,633,262 | A | | 5/1997 | Hong et al. ................. 514/300 |
| 5,776,944 | A | * | 7/1998 | Hong et al. ................. 514/300 |
| 5,869,670 | A | * | 2/1999 | Hong et al. ................. 546/123 |
| 2005/0148622 | A1 | * | 7/2005 | Choi et al. ................... 514/300 |
| 2005/0176961 | A1 | * | 8/2005 | Hayler et al. ............... 546/123 |

FOREIGN PATENT DOCUMENTS

EP 0 472 491 A1 2/1992
EP 0 478 497 A1 4/1992

(Continued)

OTHER PUBLICATIONS

Hong, et al. "Novel Fluoroquinolone Antibacterial Agents Containing Oxime-Substituted (Aminomethyl)pyrrolidines:" J. Med. Chem. 1997, 40, pp. 3584-3593.*

(Continued)

*Primary Examiner*—Kamal A. Saeed
*Assistant Examiner*—Nyeemah Grazier
(74) *Attorney, Agent, or Firm*—Ladas & Parry LLP

(57) ABSTRACT

The invention provides a process for the production of a compound of formula (I): wherein $P_1$ and $P_2$, which may be the same or different, are amino protecting groups, which comprises protection of a compound of formula (II) in solution phase continuous operation mode. This confers advantages over batch mode operation. The process is usually conducted in reaction equipment adapted for use in continuous processing mode, for example comprising one or more static mixers or a plug flow reactor. Preferably, the plug flow reactor comprises a jacketed tubular reactor fitted inside with internal mixing elements which continually split and remix the reaction streams promoting mass and heat transfer, whereby a uniform plug flow profile with turbulent fluid flow is achieved. The invention also provides a process for production of the antibacterial compound gemifloxacin or a pharmaceutically acceptable salt and/or hydrate thereof, comprising converting a compound of formula (I). The invention also provides a process for the production of a compound of formula (VIIIa)

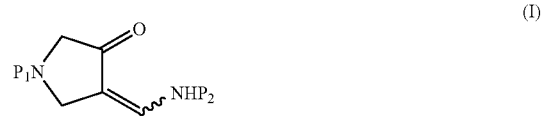

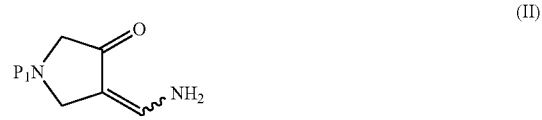

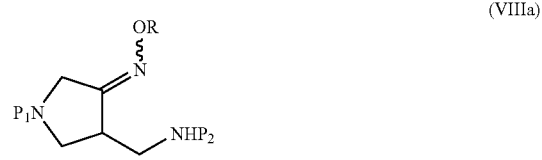

38 Claims, 13 Drawing Sheets

FOREIGN PATENT DOCUMENTS

| | | |
|---|---|---|
| EP | 0 546 989 A1 | 6/1993 |
| EP | 0 655 275 A1 | 7/1994 |
| EP | 0 646 407 A1 | 4/1995 |
| EP | 0 678 504 A2 | 4/1995 |
| EP | 0 688 772 A1 | 12/1995 |
| EP | 0 727 249 A1 | 8/1996 |
| EP | 0 749 776 A1 | 12/1996 |
| EP | 0 760 253 A1 | 3/1997 |
| EP | 0 800 857 A1 | 9/1998 |
| EP | 0 815 929 A1 | 12/1998 |
| JP | 04-368360 | 12/1992 |
| JP | 2001-081071 | 3/2001 |
| WO | 95/21173 | 8/1995 |
| WO | 98/42705 | 10/1998 |
| WO | 99/44991 | 9/1999 |
| WO | 00/17199 | 3/2000 |
| WO | 00/53282 | 9/2000 |
| WO | 01/00209 A1 | 1/2001 |
| WO | 01/15695 A1 | 3/2001 |
| WO | 01/17961 A2 | 3/2001 |
| WO | 01/18002 A1 | 3/2001 |
| WO | 01/21176 A1 | 3/2001 |
| WO | WO 200117961 A2 * | 3/2001 |
| WO | WO 200118002 A1 * | 3/2001 |
| WO | 01/32125 A2 | 5/2001 |

OTHER PUBLICATIONS

Brechtelsbauer, C., et al., "Reaction Engineering Evaluation and Utilization of Static Mixer Technology For Sythesis of Pharmaceuticals," *Organic Process Research & Development*, vol. 5, No. 6, pp. 646-651 (2001).

Henkel, K-D., "Reactor Types and Their Industrial Applications," *Ullmann's Encyclopedia of Industrial Chemistry*, vol. B4, pp. 87-120 (1992).

Hong, C.Y., et al., "Novel Fluoroquinolone Antibacterial Agents Containing Oxime-Substituted (Aminomethyl) Pyrrolidines: Sythesis and Antibacterial Activity of 7-(4-(Aminomethyl)-3-(methoxyimino)pyrrolidin-1-yl)-1-cyclopropyl-6-fluoro-4-oxo-1,4-dihydrol [1,8]napthyridine-3-carboxylic Acid (LB20304)," *J. Med. Chem.*, vol. 40, No. 22, pp. 3584-3593 (1997).

* cited by examiner

Schematic Diagram of IPFR

Comparison of Results

Schematic Diagram of Laboratory Line Mixers

Schematic Diagram of Pilot Scale Equipment

PROCESSES FOR THE PRODUCTION OF AMINO-PROTECTED DERIVATIVES OF 4-AMINOMETHYLENE-PYRROLIDIN-3-ONE AND/OR 4-AMINOMETHYLENE-PYRROLIDIN-3-ALKOXYIMINO DERIVATIVES AND/OR GEMIFLOXACIN OR A SALT THEREOF

This application is a 371 of PCT/GB02/03585, filed on Aug. 2, 2002, which claims benefit under 35 USC 119(a–d) to foreign applications United Kingdom 0118938.0, filed Aug. 2, 2001 and to United Kingdom 0217637.8, filed Jul. 30, 2002.

The present invention relates to novel processes for the production of compounds which are themselves of use in the production of pharmaceutically active compounds, for example, quinolone carboxylic acid derivatives such as gemifloxacin having antibacterial activity. In particular, the present invention relates to a process for the production of inter alia amino-protected derivatives of 4-aminomethylene-pyrrolidin-3-one; a process for the production of 4-aminomethyl-3-methoxyimino-pyrrolidine or a salt thereof or oxime-substituent variants thereof; and processes for the production of gemifloxacin or a pharmaceutically acceptable salt and/or hydrate thereof for exmaple including performing one of the aforementioned processes.

EP 0 688 772 A1 and B1 disclose novel naphthyridine carboxylic acid derivatives having antibacterial activity, including anhydrous (R,S)-7-(3-aminomethyl-4-methoxy-imino-pyrrolidin-1-yl)-1-cyclopropyl-6-fluoro-4-oxo-1,4-dihydro-1,8-naphthyridine-3-carboxylic acid. The syn oxime isomer, (R,S)-7-(3-aminomethyl-4-syn-methoxy-imino-pyrrolidin-1-yl)-1-cyclopropyl-6-fluoro-4-oxo-1,4-dihydro-1,8-naphthyridine-3-carboxylic acid, has the approved (generic) name "gemifloxacin", and has the formula:

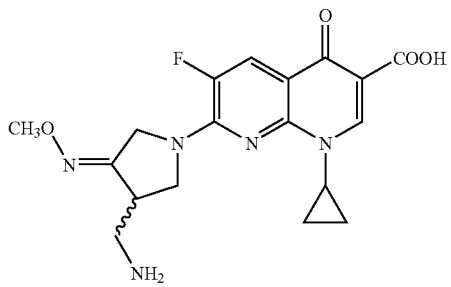

WO 98/42705 discloses (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate (gemifloxacin methanesulfonate or mesylate) and hydrates thereof including the sesquihydrate.

WO 99/44991 (PCT/KR99/00099) discloses a process for the production of 4-aminomethyl-3-alkoxyiminopyrrolidines and salts thereof from aminomethylpyrrolidin-3-one and the corresponding alkoxylamine.

A key step in the synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid is the protection of the enamino pyrrolidinone with e.g. t-butoxycarbonyl anhydride (Boc$_2$O). The batch-mode process described in WO 99/44991 (PCT/KR99/00099, see especially Examples 4, 5 and 6) involves treating a cooled suspension of 1-(N-t-butoxycarbonyl)-4-aminomethylene-pyrrolidin-3-one (obtained by Raney nickel reduction of the cyanopyrrolidinone) in e.g. isopropanol, THF or toluene, with a solution of t-butoxycarbonyl anhydride in e.g. isopropanol or THF, and with a base such as lithium t-butoxide or aqueous sodium hydroxide solution. After workup, quenching with hydrochloric acid and layer separation to remove inorganic salts, the product is recrystallised to afford 1-(N-t-butoxycarbonyl)-4-(N-t-butoxycarbonyl)aminomethylene-pyrrolidin-3-one. The reaction is shown schematically thus:

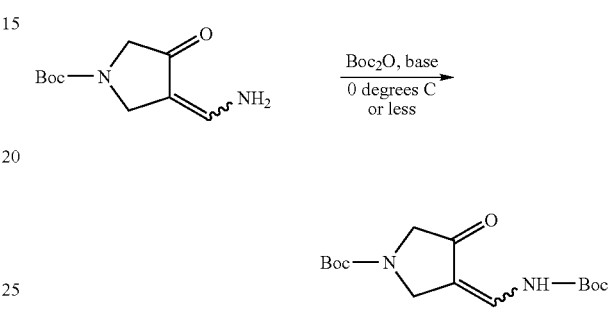

However, this reaction has several potential problems that make the batch-mode operation less than ideal, particularly on a commercial scale. The reaction has been found to have extremely fast kinetics and is characterised by being extremely exothermic. To ensure a high yield of quality material on scale up of this process precise control of several factors e.g. addition time, addition rate, temperature, reaction time, stoichiometry, reagent concentration, etc, is required, as undesired by-products (degradants, dimers and oligomers) can be generated very easily. Furthermore, the procedure is made more complex as both the product, the starting material and even the t-butoxycarbonyl anhydride are unstable under the basic reaction conditions. For example the enamine ketone and the product will undergo base hydrolysis to give the corresponding enol and this can lead to the formation of uncharacterised oligomers. Dimer/by-product formation prevents crystallisation of the product thereby reducing the isolated yield. Hence, there is a need to develop alternative methods for the production of amino-protected derivatives of 4-aminomethylene-pyrrolidin-3-one which are suitable for use on a commercial scale.

The present invention relates to a novel process for the production of amino-protected derivatives of 4-aminomethylene-pyrrolidin-3-one which are of use in the synthesis of pharmaceutically active compounds.

According to a first aspect of the invention there is provided a process for the production of a compound of formula (I):

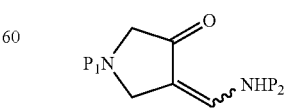

wherein P$_1$ and P$_2$, which may be the same or different, are amino protecting groups, which comprises protection of a compound of formula (II):

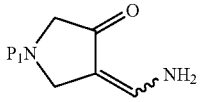

in solution phase continuous operation mode.

The C=C double bond in formula (I) and/or (II) can be in any configuration; e.g. E or Z or a mixture of E and Z. When this process is used in the synthesis of gemifloxacin or a salt thereof, these E/Z ratio are not usually important as this C=C double bond is usually reduced in the next step of the synthesis.

The first aspect of the invention also provides a process for the production of a compound of formula (IA):

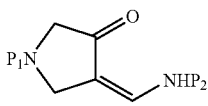

wherein $P_1$ and $P_2$, which may be the same or different, are amino protecting groups, which comprises protection of a compound of formula (IIA):

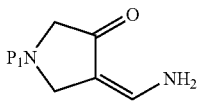

in solution phase continuous operation mode. In this specification, references to a compound of formula (I) or (II) are deemed to refer to/apply to: a compound of formula (I) or (II) respectively; and/or a compound of formula (IA) or (IIA) respectively.

"Continuous operation mode", also called "continuous processing mode", can be defined as the bringing together of two or more streams of reagents/starting materials to form a new product, in this case amino-protected derivatives of 4-aminomethylene-pyrrolidin-3-one, the compound of formula (I).

Protecting groups $P_1$ and $P_2$ include any suitable amino protecting groups, the amino protecting groups are preferably removable by acidic conditions e.g. by treatment with methanesulfonic acid. Examples of protecting groups include formyl, acetyl, trifluoroacetyl, benzoyl, para-toluenesulfonyl, methoxycarbonyl, ethoxycarbonyl, t-butoxycarbonyl, benzyloxycarbonyl, para-methylbenzyloxycarbonyl, trichloroethoxycarbonyl, beta-iodoethoxycarbonyl, benzyl, para-methoxybenzyl, trityl, tetrahydropyranyl and pivaloyl. Particular protecting groups that may be mentioned include acetyl, t-butoxycarbonyl and pivaloyl. The preferred protecting group for both $P_1$ and $P_2$ is t-butoxycarbonyl.

Protection of the amino group may be performed by reacting the compound of formula (I) with a reagent for introducing the amino-protecting group $P_2$, in the presence of a base, e.g. selected from the group consisting of lithium t-butoxide, lithium isopropoxide, potassium t-butoxide, sodium t-butoxide and lithium chloride, sodium hydroxide and potassium hydroxide. The base is preferably potassium hydroxide. The base is preferably in aqueous solution. The base, e.g. sodium or potassium hydroxide e.g. an aqueous solution thereof, is preferably used in excess relative to the compound of formula (II) e.g. at a stoichiometry of 2.5 to 4 equivalents, or ≧4 or ≧5 equivalents, relative to the compound of formula (II). However, in an alternative embodiment; and especially but not exclusively where static mixers are used comprising one or more helically-twisted mixing elements arranged axially within and in static relation to a tube (tubular reactor), e.g. "Kenics® KM-type" static mixers as described below, and/or where residence times are about 5 to about 60 seconds, preferably 10 to 30 seconds; then preferably the base is used at a stoichiometry of ≧5 or ≧6 equivalents, preferably 5 to 15, 5 to 12 or 6 to 12 equivalents, more preferably 5 to 7 or 6 to 7 equivalents, most preferably about 6 equivalents, relative to the compound of formula (II). Such a large number of equivalents is desirable to improve conversion where short residence times are used, e.g. as is typicaly the case with a "Kenics® KM-type" mixer and similar static mixers, cf. the batch mode reaction usually takes at least 30 minutes.

The reagent for introducing the amino-protecting group may be selected from the group consisting of, for example, t-butoxycarbonyl anhydride, pivaloyl chloride and acetyl chloride.

When $P_2$ is t-butoxycarbonyl the protection of the compound of formula (II) is preferably achieved by reaction with t-butoxycarbonyl anhydride in the presence of potassium hydroxide e.g. aqueous potassium hydroxide solution.

In the continuous operation mode of the invention, preferably a stream of aqueous base, e.g. potassium hydroxide, and a stream of a solution of 1-(N-protected)-4-aminomethylene-pyrrolidin-3-one of formula (II) containing the reagent for introducing the amino-protecting group, e.g. t-butoxycarbonyl anhydride, are brought together prior to quenching in acid, e.g. hydrochloric acid or preferably aqueous acetic acid. This is a two-stream system. Preferably, the acid quench is a mixture of acetic acid, water and isopropanol, more preferably about 2:1:1 by volume.

In an alternative embodiment of the continuous operation mode of the invention, a first stream of aqueous base, e.g. potassium hydroxide, a second stream of a solution of 1-(N-protected)-4-aminomethylene-pyrrolidin-3-one of formula (II), and a (separate) third stream containing (e.g. in solution) the reagent for introducing the amino-protecting group, e.g. t-butoxycarbonyl anhydride, are brought together prior to quenching in acid, e.g. hydrochloric acid or preferably aqueous acetic acid.

In all systems, it is strongly preferable that one or both of the 1-(N-protected)-4-aminomethylene-pyrrolidin-3-one of formula (II) and the reagent for introducing the amino-protecting group, e.g. t-butoxycarbonyl anhydride, are not stored in the presence of base prior to the continuous operation mode protection process of the invention.

The choice of solvent for the reaction will depend on the particular reagents used. When a base such as potassium hydroxide is used, the solution of 1-(N-protected)-4-aminomethylene-pyrrolidin-3-one of formula (I), optionally containing the reagent for introducing the amino-protecting group, is preferably an isopropanol/water solution. An alternative solvent is THF/water. These solvent sytems are also suitable where a (separate) third stream comprising a solution of the reagent for introducing the amino-protecting group is used. When a solution of 1-N-protected)-4-aminomethylene-pyrrolidin-3-one of formula (I) and/or of the reagent for introducing the amino-protecting group, is an isopropanol/water solution, then preferably it is a solution in about 20:1 to about 1:1 v/v isopropanol:water or about 10:1 to about 1:1 v/v isopropanol:water, more preferably about 10:1 to about 2:1 v/v isopropanol:water or about 8:1 to about 3:1 v/v isopropanol:water, most preferably about 5:1 v/v isopropanol:water. With this most preferred solvent mixture, the Boc anhydride is readily soluble and stays soluble on cooling. When the isopropanol concentration is raised too far, then this may decrease the solubility of any hydroxide base during the reaction.

The process (protection process) of the first aspect of the invention is preferably carried out using THF/water or more preferably isopropanol/water as solvent. Preferably, the protection process is carried out using as solvent: about 10:1 to about 1:2 v/v isopropanol:water or about 5:1 to about 1:2 v/v isopropanol:water, more preferably about 3:1 to about 2:3 v/v isopropanol:water or about 2:1 to about 1:1 v/v isopropanol:water, most preferably about 5:3 to about 5:4 v/v isopropanol: water. In general, these reaction solvent systems maximise the solubility during the reaction of: the compound of formula (II) especially where $P_1=P_2=$Boc, the reagent for introducing $P_2$, and the base.

The process of the invention is preferably conducted at a temperature of less than 20° C., preferably at a temperature of about −30 to less than 20° C., more preferably about −25 to about 10° C. or about −20 to about 10° C., still more preferably about −25 to about 0° C. or about −20 to about 0° C., even more preferably about −15° C. to about 0° C.

The process for the production of a compound of formula (I), according to the invention, may be conducted in any reaction equipment adapted for use in continuous processing mode (continuous operation mode). Continuous processing, being operated usually in steady state mode, usually offers the advantages of small reaction inventory and improved control of operating conditions. Enhanced mass transfer (mixing) and heat transfer ensure that substantially no concentration or temperature gradients exist.

The reaction equipment adapted for use in continuous processing (continuous operating) mode preferably comprises a substantially tubular reactor to form the product of formula (I) and in which or upstream of which two, three or more streams of the reagents/starting materials are brought together. The substantially tubular reactor is preferably straight but may be otherwise e.g. in the form of a coil. The tubular reactor (housing) is preferably made of metal, e.g. steel or a metal alloy containing 1, 2, 3 or more of Fe, Ni, Cr, Mo; preferably a Fe—Ni—Cr—Mo alloy such as SS316. SS316 alloy material is well-known to the skilled person. During the continuous operation mode process, the substantially tubular reactor (e.g. the jacket temperature thereof) is preferably at a temperature of less than 20° C., preferably about $\geq$ about 40, $\geq$ about −30, $\geq$ about −23, $\geq$ about −20, or $\geq$ about −15° C., preferably $\leq$ about 0° C., $\leq$ about −5, or $\leq$ about −15° C.; for example about −23 to about 0° C., about −23 to about −5° C., about −23 to about −15° C. (e.g. about −20° C.) or about −15° C. to about −5° C. or about −15 to about 0° C. The ideal reactor temperature may depend on the apparatus and conditions used (e.g. see the Examples). The tubular reactor may be provided with a jacket adapted to receive circulating fluid (e.g. liquid such as silicone oil) during use operating to control the temperature of, e.g. cool, the tubular reactor. Alternately, in use, the reactor may be cooled by immersion e.g. submerging in a coolant bath, for example containing ice/water or ice/salt water (about 0° C. or less) or ethylene glycol (e.g. about −15° C.).

Suitable reaction equipment will be apparent to those skilled in the art and includes plug flow reactors, cascades of stirred tanks (>2 CSTR's), static mixers, oscillatory flow reactors. In this equipment, mixing is induced either passively through the fluid flow (e.g. static mixer, plug flow reactor) or actively through mixing devices (e.g. CSTR's in cascade, oscillatory flow reactor). For example, see those described in Stonestreet P. Van der Veeken P M J, "The effects of oscillatory flow and bulk flow components on residence time distribution in baffled tube reactors", Chemical Engineering Research & Design. 77(A8):671–684, 1999 November; Streiff, F. A.; Rogers, J. A.; "Don't overlook static mixer reactors", Chem. Eng. (N.Y.) 101, 6 (1994), 76–82; and Levenspiel, O.; Chemical Reaction Engineering, Wiley, N.Y., 1993.

Equipment such as plug flow reactors or static mixers are non back-mixed systems, which provide substantially no axial diffusion and substantial (good) radial homogeneity. Oscillatory flow reactors are partly back-mixed systems. The mixing time in the equipment is preferably shorter than the reaction half life, which is the time required to reach 50% conversion, so that the reaction is in a kinetically controlled regime. Residence time can then be adjusted to reach the required conversion.

One approach uses a plug flow reactor being an Intensified Plug Flow Reactor Rig (IPFR), e.g. as shown schematically in FIG. 1. Efficient mixing is necessary for a successful reaction, the IPFR offers benefits with respect to reaction rate and selectivity. A typical IPFR comprises a substantially tubular reactor, preferably a jacketed tubular reactor, fitted with internal mixing elements, e.g. Sulzer® SMV mixing elements; as described above, mixing is induced passively through the fluid flow. The mixing elements inside the pipe continually split and remix the reaction streams promoting mass and heat transfer. Thus, even for low flow-rates and Reynolds numbers, a uniform plug flow profile with turbulent fluid flow can be achieved. The jacket of the jacketed tubular reactor is preferably adapted to receive circulating fluid (e.g. liquid such as silicone oil) during use operating to control the temperature of, e.g. cool, the tubular reactor.

The use of the Intensified Plug Flow Reactor or IPFR has been described in C. Brechtelsbauer and F. Ricard, *Organic Process Research & Development*, 2001 (November), 5, 646–651, published on 27 Oct. 2001 on the internet. The contents of this reference, especially but non-exclusively the theory and experimental results regarding residence time, Bodenstein number, heat transfer, kinetics, etc, are incorporated herein by reference.

Whether for plug flow or static mixers, the internal mixing elements may project inwardly from the inner circumferential surface of the tubular reactor and/or the internal mixing elements may be integrally formed with the inner circumferential surface of the tubular reactor, but preferably one or more (preferably most or all) of the internal mixing elements comprise an one or more inserts insertable into the inside of the tubular reactor and capable of being positioned in substantially fixed (static) relation to the reactor.

Sulzer static mixing elements/static mixers/plug flow reactors are obtainable from Sulzer Chemtech (UK) Ltd, Westmead, Farnborough, Hampshire GU14 7LP, UK, tel: +44 1252 544311; Sulzer Chemtech Ltd, Separation and Reaction Technology, P.O. Box 65, CH-8404 Winterthur, Switzerland, tel: +41 52 262 67 20; www.sulzerchemtech.com. For example, the following mixing elements/mixers are suitable: the Sulzer® SMV mixer; the Sulzer® SMR mixer-reactor; or possibly the Sulzer® SMXL mixer-heat exchanger, e.g. as shown in http://www.sulzerchemtech.com/eprise/SulzerChemtech/Sites/products_services/static-Mixers/mixers.html and Sulzer Chemtech's Mixing and Reaction technology catalogues. Sulzer® SMV mixers may require a longer reaction time than the Kenics® KM-type static mixer described below, but are highly suitable and effective for large quantities and turbulent/plug flow conditions.

Preferably, one or more (e.g. most or all) of the static mixers or the plug flow reactor comprises one or more static mixing elements, wherein some, most or all of the mixing elements comprise a plurality of (e.g. about 3, 4, 5 or 6) stacked corrugated sheets, wherein the grooves of each corrugated sheet are transverse to, more preferably substantially perpendicular to, the grooves of any directly adjacent corrugated sheet (e.g. the sheet directly above and the sheet directly below). "Stacked" in this context means "flat-stacked", i.e. the grooves of the corrugated sheets are directed generally towards (i.e. generally face) the grooves of any directly adjacent corrugated sheet; one example of this arrangement is shown in FIGS. 6 to 9 (Sulzer® SMV mixing element—"Sulzer SMV-type"). In the generalised mixing element, the plurality of stacked corrugated sheets splits and mixes the fluid stream width-wise across the sheets; so that in more general terms one or more (e.g. most or all) of the static mixers or the plug flow reactor comprises one or more static mixing elements, wherein some, most or all of the mixing elements are adapted to split and mix a fluid stream flowing therethrough substantially in one dimension transverse to the fluid flow.

Preferably, the mixing elements are substantially cylindrical in outside profile so as to fit snugly within the tubular reactor, with the cylinder axis being substantially parallel to the planes of the corrugated sheets.

Preferably, a plurality of the mixing elements (e.g. 3, 4, 5 or more) are substantially axially aligned within the substantially tubular reactor, with the corrugated sheets arranged so as to allow fluid flow longitudinally along the tubular reactor. Adjacent mixing elements are preferably in contact with each other, and are usually not attached or fused to each other, but some, most or all of the mixing elements optionally can be attached or fused into a unitary composite mixing structure. Mixing elements are preferably kept in approximately static relation to the tubular reactor by mixing-element fixing means. The fixing means can be an open end cap (e.g. S-shaped) fixable or fixed across one or both ends of the tubular reactor capable of allowing fluid flow therethrough and capable of holding and/or compressing the mixing elements together within the tubular reactor. Preferably, some or all of the mixing elements in the tubular reactor are statically arranged so as to be in a rotated orientation (preferably rotated substantially perpendicularly e.g. by 70–110° e.g. by about 90°) about the longitudinal axis of the tubular reactor relative to one or both of the neighbouring mixing elements. Preferably, each mixing element is turned by 90° about the longitudinal axis relative to the mixing element on either side of it; one example of such an arrangement of the mixing elements in the tubular reactor is shown in FIG. 10. Here, the first element splits and mixes the stream from side to side, the second element splits and mixes the stream in an up-down direction, the third element splits and mixes the stream side to side, etc. Sulzer® SMV mixing elements and static mixers are of this type ("Sulzer SMV-type").

This arrangement ensures good efficient and rapid mixing and splitting of streams in both directions and is suitable for turbulent/plug flow and/or immiscible liquid streams. For example, for the protection process of the invention according to Examples 1–5, the aqueous KOH stream and the isopropanol/water stream containing both Boc$_2$O (Boc anhydride) and the compound of formula (II) where P$_1$ is t-butyloxycarbonyl are usually initially miscible, but salt formation during the reaction causes a change in the density of the aqueous stream which can cause the IPA-containing stream and aqueous stream to split (i.e. become immiscible) during the reaction in the absence of efficient and rapid mixing elements in the tubular reactor.

An alternative but similar approach to the IPFR is to incorporate one or more static mixers to obtain the required mixing, e.g. as shown schematically in FIG. 3. Two streams can be brought together and then passed through a static mixer or a series of static mixers, e.g. Kenics® static mixers (e.g. length 20 cm, od 0.5 cm, id 0.33 cm), in particular Kenics® KM static mixers. The outlet from the one or more static mixers preferably passes into an acid quench. The number of mixers used is dependant up on the dimensions of the mixer, the flow rate and efficiency of mixing.

Kenics® static mixers are obtainable from: Chemineer, a unit of R&M Ltd., Cranmer Road, West Meadows, Derby DE21 6XT, United Kingdom; or Chemineer, Inc., 125 Flagship Drive, North Andover, Mass. 01845, USA (see also http://www.chemineer.com/main.php for general information and . . . /km.php for Kenics® KM static mixers).

In the static mixer embodiment, preferably, one or more (e.g. all) of the static mixers comprise one or more mixing elements arranged (or capable of being arranged) substantially axially within and in substantially static relation to a substantially tubular reactor, and the mixing elements define at least one substantially helical fluid flow path in the axial direction between the mixing element and the inner circumferential walls of the tubular reactor. These are herein named "Kenics® KM-type" static mixers. Preferably, two or more substantially helical fluid flow paths are so defined. Preferably, the mixing elements are helically-twisted about their axis so as to define the at least one substantially helical fluid flow path. Usually, one or more (e.g. all) of the static mixers comprise one or more helically-twisted mixing elements arranged axially within and in substantially static relation to substantially tubular reactor; usually they comprise a series of alternating right- and left-handed helically-twisted mixing elements, i.e. having alternating rotational directions.

Preferably, each or most mixing element(s) is/are a plate, preferably with about 180° of helical twist. Preferably, a leading edge of each element is located substantially perpendicularly (e.g. at about 90°) to a trailing edge of the following element. As the fluids pass through each element, they are usually divided by the power of two since each successive element is offset by about 90°. One example of this arrangement is shown in FIGS. 11 and 12. The series of alternating right- and left-handed helical structure improves radial mixing by giving the fluid element radial and angular momentum. The helical twist angle, offset angle, width and height of the mixing element may vary depending on the property of feed. These "Kenics® KM-type" static mixers improves the speed of mixing and gives a higher surface to volume ratio than a tank reactor which is usually used in batch-mode reaction.

Adjacent "Kenics® KM-type" mixing elements are preferably in contact with each other when in the reactor. Optionally, some, most or all of the mixing elements may be attached or fused to each other to form a unitary composite mixing structure; e.g. there is one unitary composite mixing structure per tubular reactor and/or the composite mixing structure is optionally insertable into the inside of the reactor (e.g. see Kenics static mixing technology catalogue for fused mixing structure examples).

Preferably, for these "Kenics® KM-type" static mixers, the tubular reactor has an internal diameter of about 0.1 to about 10.0 cm and/or ≧0.33 cm, preferably 0.33 to about 3.0 cm, more preferably 0.33 to about 1.3 cm internal diameter. A too large diameter may give difficulties removing the heat of reaction sufficiently, and a too small diameter gives productivity and throughput difficulties. Preferably, the tubular reactor (housing) and/or the mixing elements are made of metal, e.g. steel or a metal alloy containing 1, 2, 3 or more of Fe, Ni, Cr, Mo; preferably a Fe—Ni—Cr—Mo alloy such as SS316.

These "Kenics® KM-type" static mixers are available from Chemineer at the above contact addresses, and are described (a) on Chemineer's internet site given above and (b) in Chemineer, Inc.'s "Kenics static mixing technology" brochure, 1998 available by post or via the internet site. They have also been described in "Applied Process Design for Chemical and Petrochemical Plants" by Ernest E. Ludwig, $2^{nd}$ Edition, Volume 1, Gulf Publishing Company, 1977, see e.g. on and around page 203.

In a preferable embodiment, a plurality of (e.g. 2–10, e.g. 3–8, most preferably about five) static mixers, e.g. "Kenics® KM-type" static mixers, are connected in series. Preferably, some, most or all of the "Kenics® KM-type" static mixers contain 4–100 or 6–50 or 10–40 or most preferably about 27 "Kenics® KM-type" mixing elements. It is the total number of Kenics elements that is important, and/or the total length of the reaction path in the plurality of mixers; the number of static mixer units can be varied according to the number of elements each static mixer unit has. Therefore the reaction equipment adapted for use in the continuous processing mode process preferably comprises 20–400, 40–300, 70–200, 90–180 or about 135 "Kenics® KM-type" mixing elements arranged in series within one or more substantially tubular reactors. The total number of elements also can vary with the mixing performance per element, which depends on the size of the element and the flow rate used.

Other types of static mixer/mixing elements which might possibly be usable in the continuous processing mode of the invention include: dispersive/distributive static mixer, KAM static mixer, wafer type static mixer, Komax static mixer, Kenics HEV type static mixer; and mixers/mixing elements published in: EP 0 472 491 B1, EP 0 478 497 B1, EP0546989 B1, EP0655275 B1, EP0749776 B1, EP0727249 B1, EP0760253 B1, EP 0800 857 A1, EP 0815929 B1 (all Sulzer Chemtech AG).

The two, three or more streams of the reagents/starting materials may be brought together in a or the reactor (e.g. the substantially tubular reactor) (see for example Example 6), or may optionally be brought together upstream of the reactor by various stream-mixing means. The optional stream-mixing means may be a three-way, four-way or other junction.

The stream-mixing means may optionally be a direct junction which contains substantially no mixing chamber (i.e. has a low dead-volume) at the junction. This preferably is a three-way direct junction i.e. a "T-piece" which includes T- and Y-shaped and other shaped pieces. See for example FIG. 3A and Example 3.

Alternatively, the stream-mixing means may comprise a substantial mixing chamber having two, three or more reagent inlets in fluid communication with the stored reagents and an outlet in fluid communication with the reactor (e.g. the substantially tubular reactor). When the stream-mixing means comprises a substantial mixing chamber, then preferably the stream-mixing means is a vortex mixer adapted to mix at least partly the reagent streams in use by generation of a vortex in the mixing chamber and/or in the outlet (this might only achieve a partial mixing). Preferably, the vortex mixer has a substantially cylindrical mixing chamber (e.g. a substantially disc-shaped, i.e. substantially flat-cylindrical, mixing chamber) and the outlet is substantially axially disposed. More preferably, the reagent inlets are arranged at or adjacent the circumference of the cylindrical chamber and for example are directed substantially tangentially at or adjacent the circumference. See for example Example 9 and FIGS. 13 and 14. Details of suitable vortex mixers are disclosed in Example 9 hereinafter, and the following references incorporated herein by reference: WO 95/21173 A1 (FIGS. 1A and 1B), WO 00/53282 (see FIG. 1 and page 2 line 18 to page 3 line 5 and especially the mixing chamber dimensions given therein); see also WO 01/32125 A2 (FIG. 6 and pages 12–13) and EP 0 646 407 A1.

The stream-mixing means is preferably made of metal, e.g. steel such as stainless steel or a metal alloy containing 1, 2, 3 or more of Fe, Ni, Cr, Mo; preferably a Fe—Ni—Cr—Mo alloy such as SS316.

In use, the stream-mixing means, e.g. the direct junction or vortex mixer, is preferably at a temperature of less than 20° C.; preferably about $\geq$ about 0, $\geq$ about –30, $\geq$ about –23, $\geq$ about –20, or $\geq$ about –15° C.; preferably $\leq$ about 0° C., $\leq$ about –5, or $\leq$ about –15° C. The stream-mixing means may be cooled by immersion e.g. submerging in a coolant bath, for example containing ice/water or ice/salt water (about 0° C. or less) or ethylene glycol (e.g. about –15° C.).

Using the continuous operation process of the invention it is possible to obtain conversions in excess of 95%, the reaction often being complete within 10–30 seconds (with "Kenics® KM-type" static mixers, longer with Sulzer SMV mixing elements), and, importantly, substantial reduction in degradation and dimer/oligomer formation compared to the batch mode procedure, resulting in an increase in the isolated yield of the material compared to the batch mode procedure.

It is also possible to extend the continuous nature of the process to incorporate the workup/isolation into a continuous mode, including some of the up stream and downstream reactions. For example, continuous work up/post processing. continuous quenching by adding a quench stream, implementing a continuous separator and/or a continuous crystalliser and dryer.

The residence time (retention time) can be about 1 second to about 30 minutes or about 5 seconds to about 20 minutes. The residence time can be about 5 to about 2 minutes or about 5 to about 60 seconds, preferably 10 to 30 seconds, especially when static mixers are used comprising one or more helically-twisted mixing elements arranged axially within and in static relation to a tube (tubular reactor), e.g. "Kenics KM-type" static mixers, e.g. as shown in Table 4 in Example 2 (residence times 10, 20 and 30 seconds) and Examples 2–4. Alternatively, especially for static mixers or plug flow reactors comprising one or more static mixing elements wherein each mixing element comprises a plurality of stacked corrugated sheets and wherein the grooves of each sheet are transverse to the grooves of any sheet directly above and to the grooves of any sheet directly below ("Sulzer SMV-type"), then the residence time can be about 1 minute to about 20 minutes, e.g. about 3 to about 20 minutes, e.g. about 4.8 minutes or about 13 minutes e.g. as shown in Table 2 in Example 1.

The compounds of formula (II) may be prepared by the processes described in U.S. Pat. No. 5,633,262, EP 688772A1 and WO 99/44991 (PCT/KR99/00099).

The compounds of formula (I) are useful as an intermediates for preparing quinolone antibacterials particularly those described in U.S. Pat. No. 5,633,262 and EP 688772A1 (e.g. see Example 180 of EP 688772A1 for gemifloxacin with an undefined oxime sterochemistry). Gemifloxacin, the compound of formula (III) below, is indicated for the treatment of respiratory tract infections such as community acquired pneumonia, acute exacerbations of chronic bronchitis and acute sinusitis; uncomplicated urinary tract infections; and for the treatment of bacterial infections as disclosed in EP 688772A1, WO 01/00209 A1, WO 01/15695 A1, and WO 01/21176 A1.

Thus according to a second aspect of the invention there is provided a process for the production of a compound of formula (III), or a pharmaceutically acceptable salt and/or hydrate thereof:

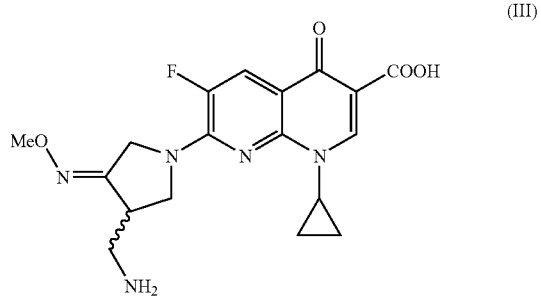

(III)

which comprises:

optionally producing a compound of formula (I) according to a process described in the first aspect of the invention herein; and converting a compound of formula (I) to a compound of formula (IV):

(IV)

or a salt thereof, preferably the dimethanesulfonate for example as described in WO01/17961, followed by reaction of the compound of formula (IV) or a salt thereof, with a compound of formula (V):

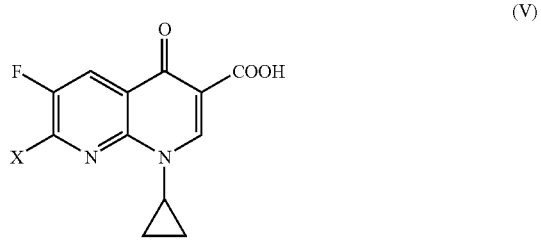

(V)

wherein X is a leaving group, e.g. a halogen atom, preferably chlorine, for example as described in WO01/1 8002 (in the presence of a base and an aqueous solvent such as acetonitrile/water or water); and optionally forming a pharmaceutically acceptable salt and/or hydrate thereof.

Other suitable leaving groups X will be apparent to those skilled in the art.

The compound of formula (I) may be converted to a compound of formula (IV) by selective reduction of the double bond carried out using a metal catalyst, e.g. a transition metal catalyst, such as Raney-nickel, palladium-carbon or Lindlar's catalyst, followed by reaction with a compound of formula (VI):

Me-ONH$_2$ (VI)

or a salt thereof (e.g. the HCl salt, Me-ONH$_2$.HCl) followed by deprotection of the amino groups, and, optionally, salt formation. These processes are for example described in WO 99/44991 (PCT/KR99/00099, e.g. Examples 7 and 8 and Reference Example 1) and partially so in EP 0 688 772 A2 (e.g. Preparations 51 and 54). Alternatively or additionally, the compound of formula (I) can be converted to a compound of formula (IV) or the salt thereof according to the third and/or fourth aspects of the invention as hereinafter described.

The reaction of the compounds of formulae (IV) and (V) is preferably conducted in the presence of a base e.g. triethylamine. Further details regarding the reaction of the compounds of formula (IV) and (V) can be found in U.S. Pat. No. 5,633,262 and EP 688772A1. The compounds of formula (V) may be synthesisied as described in U.S. Pat. No. 5,633,262 and EP 688772A1.

The compound of formula (III) produced according to this aspect of the invention is preferably (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or a hydrate thereof, preferably the sesquihydrate, as disclosed in WO 98/42705. The methanesulfonate and hydrates thereof may be synthesised from the free acid as described in WO 98/42705 and WO 00/17199.

A further aspect of the invention provides a compound of formula (III), or a pharmaceutically acceptable salt and/or hydrate thereof, (a) obtainable by, or (b) which has been (whenever) obtained (produced) by, a process according to the second aspect of the invention.

In a third aspect of the invention, it has also separately been discovered that the oxime compound of formula (VIII),

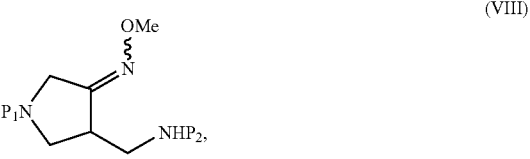

(VIII)

which is formed during the reaction of Me-ONH$_2$ (VI) or a salt thereof with 1-(N-protected)-4-(N-protected)aminomethyl-pyrrolidin-3-one in the synthesis of gemifloxacin, is often quite unstable. Compound (VIII), wherein $P_1$=$P_2$=t-butoxycarbonyl ("AM08"), is usually a liquid or oil e.g. as implicitly disclosed in Reference Example 1 in page 19 line 3 of WO 99/44991. If (VIII), wherein $P_1$=$P_2$=t-butoxycarbonyl, is isolated by solvent removal it has now been discovered that there is a risk of decomposition especially at large scale where a long period of heating is usually required to remove solvent. A method of mitigating this problem has now been discovered.

Also, separately, the three-step conversion of (I) to (IV) or a salt thereof when $P_1$=$P_2$=t-butoxycarbonyl is known from WO 99/44991 A1 (e.g. Example 7 or 8 plus first part of Reference Example 1); and an alternative third step of deprotecting (VIII) to (IV) as the di-mesylate salt is known from WO 01/17961 A2 (e.g. Examples 1 or 2). These 3-step process is time-consuming, especially the distillation removal of tetrahydrofuran solvent in the first step Example 8 of WO 99/44991 A1; this and other published aspects reduce throughput especially on a on large scale. In a preferable embodiment of the third aspect of the invention, a method has been discovered which mitigates this time/throughput problem.

Accordingly, a third aspect of the invention provides a process for the production of a compound of formula (IV):

(IV)

or a salt thereof, preferably the dimethanesulfonate salt thereof, comprising the steps of:
(i) optionally reducing a compound of formula (1):

(I)

wherein $P_1$ and $P_2$ are amino protecting groups as defined herein, to a compound of formula (VII):

(VII)

wherein $P_1$ and $P_2$ are as defined in formula (I), in the presence of a first organic solvent;
(ii) reacting the compound of formula (VII) with a compound of formula (VI):

Me-ONH$_2$ (VI)

or an acid addition salt thereof (e.g. the HCl salt, Me-ONH$_2$.HCl) in the presence of a second organic solvent, to form a compound of formula (VIII):

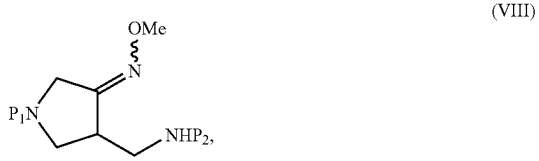

(VIII)

wherein $P_1$ and $P_2$ are as defined in formula (I); followed by
(iii) removing the amino protecting groups $P_1$ and $P_2$ of the compound of formula (VIII) in the presence of a third organic solvent and a deprotecting agent capable of performing this removal, to form the compound of formula (IV) or the salt thereof;

characterised in that, after formation of the compound of formula (VIII) in step (ii), part or all of the second organic solvent is removed and replaced by the third organic solvent without isolation of the compound of formula (VIII).

"Without isolation" of a compound from a reaction is herein defined as meaning without substantial crystallisation of the compound from the reaction solution and without the compound being otherwise reduced to a substantially solvent-free or solvent-depleted state (an oil containing a small amount of solvent being regarded as being solvent-depleted). The reaction solvent can be removed "without isolation" of the compound e.g. if a solvent "switch" takes place, i.e. if part, most or substantially all of the reaction solvent is removed after addition of one or more batches of a solvent usually a different solvent and more preferably the solvent for the subsequent reaction.

Preferably, after formation of the compound of formula (VIII) in step (ii), most or all, more preferably substantially all or all, of the second organic solvent is removed and replaced by the third organic solvent without isolation of the compound of formula (VIII).

Preferably, the compound of formula (IV) or the salt thereof is the dimethanesulfonate salt thereof, for example as described in WO01/17961 A2. The name of this compound is 4-aminomethyl-3-methoxyimino-pyrrolidinium dimethanesulfonate, also called "AM19". Also, in the third and other aspects of the invention, the compound of formula (IV) or the salt thereof produced in step (iii) can be a mixture of E- and Z-oximes (similarly the compound of formula (VIII)); but preferably step (iii) produces a predominance of the Z-oxime of the compound of formula (IV) or the salt thereof. Preferably, both $P_1$ and $P_2$ are t-butoxycarbonyl.

In the third and other aspects of the invention, if optional step (i) is carried out, then steps (i) and (ii) are preferably carried out without isolation of the compound of formula (VII). This helps to increases the ease of the reaction, decreases the total time spent to convert of (I) to (IV) e.g. on large scale, and therefore increases throughput compared to the WO 99/44991 A1 and WO 01/17961 A2 examples.

Where step (i) is carried out without isolation of the compound of formula (VII), preferably the second organic solvent is or includes some or all of the first organic solvent. Preferably, the first organic solvent is a substantially water-immiscible organic solvent which does not consist essentially of dichloromethane or optionally chloroform. Preferably, the first organic solvent comprises, consists essentially of or is ethyl acetate; the first solvent can suitably include or be toluene, xylene, and/or t-butyl methyl ether. The first organic solvent is preferably as defined below for the second organic solvent in step (ii), independent of the second organic solvent.

Optional step (i) is preferably carried out in the presence of a metal catalyst, e.g. a transition metal catalyst such as Raney-nickel or palladium-carbon, more preferably palladium-carbon. Conditions in step (i) can include one or more of the features described in pages 8–9 of WO 99/44991.

In the third and other aspects of the invention, the reaction of step (ii) is preferably carried out in the presence of water. For step (ii), it is preferable to adjust the pH to 2–9 or 2–7 if not already within this range, preferably to a pH of about 3 to about 6, more preferably to a pH of about 4 to about 5, most preferably to a pH of about 4.5. Preferably the pH is so adjusted after mixture of the compound of formula (VII)

with a compound of formula (VI). Such adjustment is in paticularly desirable where an acid addition salt, e.g. the HCl salt, of the compound of formula (VI) is used. At pH 2 or below, reaction is quick but by-products appear to be formed, as shown by new peaks in the hlpc and a darkening of the solution. At pH 7–9, the reaction works but is much slower. For step (ii), in particular where an acid addition salt of the compound of formula (VI) is used, a base is preferably present in the reaction mixture to adjust the pH to the desired range; e.g. the base is preferably an aqueous basic solution (e.g. aqueous alkali metal hydroxide solution, e.g. aqueous sodium or potassium hydroxide solution, or aqueous alkali metal (e.g. $Na^+$ or $K^+$) carbonate or hydrogen carbonate).

Preferably, especially but not exclusively where water is present during the step (ii) reaction, the second organic solvent is a substantially water-immiscible organic solvent. "Water-immiscible" means not forming at 20° C. a single-phase solvent system with water or with any aqueous phase which is present during the reaction of step (ii) or any optional aqueous work-up of step (ii). Formation of a dispersion (e.g. droplets) in water during agitation is not deemed to be water-miscibility. The first or second substantially water-immiscible organic solvent can include a minor water-miscible organic component, but must as a whole be substantially immiscible—as defined above—with water and with any aqueous phase which is present during the reaction of step (ii) or any optional aqueous work-up of step (ii). The first or second substantially water-immiscible organic solvent preferably comprises $\geq 70$ or $\geq 80$ or $\geq 90\%$ v/v of, or consists essentially of, one or more organic component(s) which are substantially water-immiscible. Preferably, the second water-immiscible organic solvent does not consist essentially of dichloromethane or optionally chloroform; preferably the first or second water-immiscible organic solvent does not consist essentially of a haloalkane. Preferably, the first and/or second substantially water-immiscible organic solvent comprises, consists essentially of or is: toluene; xylene; an ether e.g. a $C_{1-4}$alkyl $C_{1-4}$alkyl ether such as t-butyl methyl ether; and/or an ester, e.g. a $C_{1-4}$alkyl $C_{1-4}$alkanoate, a $C_{1-4}$alkyl $C_{2-4}$alkanoate, and/or a $C_{1-4}$alkyl acetate such as butyl acetate or ethyl acetate. For inter alia a superior step (ii) reaction rate at reflux, the second organic solvent most preferably comprises, consists essentially of or is ethyl acetate—this is substantially water-immiscible. Water-immiscible solvents like ethyl acetate are desirable in the oximation step (ii) to allow the excess of methoxylamine used to be washed out into an aqueous layer on aqueous work-up. Preferably, therefore, after the reaction of step (ii) is substantially complete any optional aqueous layer is removed and the second substantially water-immiscible organic solvent is then extracted one or more times with water and/or a suitable aqueous solution (e.g. aqueous salt solution e.g. aq. NaCl, KCl or $NH_4Cl$).

Step (ii) is preferably carried out at about 50–110° C. or about 60–100° C. or about 70–90° C. and/or substantially at reflux (e.g. about 70–77° C. or ca. 73° C. where the second organic solvent is ethyl acetate), preferably until the reaction is substantially complete and/or for about 1 to about 2 hrs. This gives faster completion and better throughput than the Reference Example 1 in page 18–19 of WO 99/44991 which used room temperature stirring for 3 hours.

Also, importantly, it has been discovered, at least for the salt of the compound of formula (IV) which is the dimethanesulfonate ("AM19", disclosed in WO01/17961 A2), that the compound of formula (IV) or salt thereof can sometimes be formed in an undesirably high ratio of E- to Z-oxime isomers during step (iii) of the third aspect of the invention (no isolation of the compound of formula (VIII)) when the second organic solvent is or comprises ethyl acetate. The Z-oxime is desirably predominant in AM19 at a level of at least 97.3 mol % (i.e. $\leq 2.7$ mole % v/v of E-oxime), for the purposes of synthesising gemifloxacin or salts thereof which predominantly comprise Z-oxime. However, it has been discovered that $\geq 2.7$ mole % v/v of E-oxime is formed, when a substantial amount of a solvent in which AM19 is substantially insoluble, such as ethyl acetate, is present during the deprotection of AM08 (VIII, $P_1=P_2=$t-Boc) to AM19. It has been found that, for (IV) or its salt, the E/Z-oxime isomerisation equilibrium in solution is heavily shifted towards the desirable Z-oxime at least for the AM19 dimesylate, but that this equilibrium position is only reached after some time in solution. It has also been found that the inclusion of substantial amounts of AM19-antisolvents such as ethyl acetate increases the speed of AM19 crystallisation thereby hindering equilibration and increasing levels of the undesirable E-oxime in the usual event that levels of the E-oxime are relatively high in the di-N-protected oxime of formula (VIII) such as AM08.

Therefore, to improve the AM19 or other (IV) compound or salt produced, it appears desirable to minimise the levels of ethyl acetate present during the reaction in step (iii). However, as discussed above, water-immiscible solvents like ethyl acetate are desirable in the earlier oximation step (ii) to allow the excess of methoxylamine used to be washed out into an aqueous layer, and according to the third aspect of the invention it is not desirable for decomposition reasons to remove the ethyl acetate from step (ii) in such a way as to isolate the compound (VIII) such as AM08.

Accordingly, in a preferable embodiment of the third or other aspect of the invention, the second organic solvent is an antisolvent for the compound of formula (IV) or the salt thereof which is formed in step (iii); and in step (iii) the reaction solution contains no more of the antisolvent than that amount which would lead to early crystallisation of the compound of formula (IV) or the salt thereof and/or which would increase the E/Z-oxime ratio in the compound (IV) or salt formed, compared to the crystallisation time and/or E/Z-oxime ratio obtainable with no antisolvent present. More preferably, in step (iii) the reaction solution contains $\leq 5\%$, more preferably $\leq 1\%$, still more preferably $\leq 0.2\%$ of the antisolvent by volume of pure solvent or by volume of solution (including the possibility that no antisolvent is present).

By "antisolvent" is meant any organic solvent in which the compound or salt—the compound of formula (IV) or the salt thereof which is formed in step (iii)—has a solubility at the step (iii) reaction temperature (e.g. 10–50° C., preferably 40–45° C.) of $\leq 20$ times or preferably $\leq 5$ times or $\leq 2$ times or $\leq 1.5$ times the solubility of the compound or salt at that same reaction temparature in ethyl acetate. This solubility can be measured using conventional methods or routine modifications thereof.

Preferably, the second organic solvent is an antisolvent for the compound of formula (IV) or the salt thereof, and comprises or consists essentially of or is ethyl acetate. More preferably, in step (iii) the reaction solution contains $\leq 5\%$, more preferably $\leq 1\%$, still more preferably $\leq 0.2\%$ of ethyl acetate by volume of pure solvent or by volume of solution (including the possibility that no ethyl acetate is present). This method is illustrated in Example 10, in particular steps 9) and 10). In comparison, step 9) of Example 10 has been altered by—after adding the first methanol batch—not azeotropically removing most of the ethyl acetate and adding methanol again, so that step 10) of the alternative Example used ca. 100 ml of AM08, 50 ml ethyl acetate, and 300 ml methanol in the step (iii) deprotection=ca. 11% ethyl acetate by volume of reaction solvent or ca. 14% ethyl acetate by volume of reaction solution. This alternative Example gives a successful reaction but substantially increased levels of the undesirable E-oxime i.e. an increased E/Z-oxime ratio compared to Example 10 where the ethyl acetate (second organic solvent and AM19 antisolvent) is subtantially removed.

In an alternative embodiment, the second organic solvent is not an antisolvent for the compound of formula (IV) or the salt thereof which is formed in step (iii), as herein defined. This would avoid or reduce the desirability of removing part or all of the second organic solvent before step (iii).

Preferably, in the third and other aspects of the invention, (a) the second organic solvent is different from and forms an azeotropic mixture with the third organic solvent allowing azeotropic removal of the second organic solvent from such a mixture, and/or (b) the second organic solvent is different from and has a lower boiling point (e.g. $\geq 10°$ C. lower) than the third organic solvent; and after formation of the compound of formula (VIII) in step (ii), the second organic solvent is mixed with part or all of the third organic solvent, and part or all (e.g. most or substantially all or all) of the second organic solvent is removed (e.g. azeotropically) by distillation or evacuation of the solvent mixture; followed by optionally adding a further portion of the third organic solvent before or during step (iii). In this way, part or all of the second organic solvent can be removed "without isolation" of the compound of formula (VIII) by means of a solvent "switch".

As discussed, preferably, step (iii) produces a predominance of the Z-oxime of the compound of formula (IV) or the salt thereof. More preferably at least 97.3 mole % or at least 98.5 mole % of the compound of formula (IV) or the salt thereof produced in step (iii) is the Z-oxime, preferably the dimethanesulfonate salt thereof.

Other preferable aspects of step (iii), forming the compound of formula (IV) or the salt thereof in the third or other aspect of the invention, are as follows. The reaction in step (iii) is suitably carried out at a temperature of between about 110° C. to about 50° C., more preferably at a temperature of about 40–45° C. The deprotecting agent is typically an acid, e.g. a mineral acid such as methanesulfonic acid or hydrochloric acid. The amount of methanesulfonic acid or other acid, which can be used to effect removal of the amino protecting groups $P_1$ and $P_2$ of the compound of formula (VIII), is suitably 2 to 4 equivalents. For example, about 2.4 equivalents, suitably used at a temperature of between about 35° C. to about 40° C.; or about 3 equivalents, suitably used at ambient temperature; more preferably about 2.5 equivalents suitably used at a temperature of about 40–45° C.

The reaction in step (iii) is carried out in the presence of the third organic solvent which preferably comprises, consists essentially of or is: an alcohol such as methanol, ethanol, isopropanol, or n-propanol; dichloromethane; acetonitrile; acetone; methyl iso-butyl ketone; DME; THF; tert-butylmethyl ether; dioxane; ethyl acetate or a mixture of any of these. The solvent is preferably methanol. Preferably, the third organic solvent does not comprise ethyl acetate or any other antisolvent (as defined herein) (this does not exclude the possibility that some small percentage of ethyl acetate as second organic solvent from step (ii) remains present in the step (iii) reaction, as discussed above). Suitably, up to 10 equivalents by volume of the third organic solvent may be used, e.g. about 4 equivalents.

Preferably, in step (iii), the compound of formula (IV) or salt thereof which has crystallised from the reaction mixture is re-suspended and/or re-dissolved in the third organic solvent or other suitable solvent e.g. organic solvent, and heated substantially to reflux (e.g. about 64–65° C. for methanol) and/or to about 50–110° C. or to about 50–90° C. or to about 55–80° C. or to about 60–80° C., the heating being for about 0.5 to about 4 hrs (e.g. about 1 hr) or for a time sufficient to ensure that at least 97.3 mole % or at least 98.5 mole % of the compound of formula (IV) or the salt thereof produced in step (iii) is the Z-oxime. This heating is to encourage the compound of formula (IV) or the salt thereof to further approach equilibrium between the E- and Z-oximes, and in equilibrium the desired Z-oxime is present in large excess over the E-oxime.

In the third aspect of the invention, the methyl substituent on the oxime can be replaced by other substituents. Therefore, the third aspect also provides a process for the production of a compound of formula (IVa):

(IVa)

or a salt thereof, wherein R is $C_{1-10}$ alkyl optionally fluorinated; $C_{2-6}$alkenyl; $C_{3-10}$ cycloalkyl with a 3–8-membered carbocyclic ring; $C_{6-14}$aryl; $C_{2-13}$ monocyclic, bicyclic or tricyclic heteroaryl; or $C_{6-14}$aryl $C_{1-4}$alkyl; wherein any aryl or heteroaryl moieties are optionally substituted by one, two or three of: $C_{1-3}$ alkyl optionally fluorinated, a halogen atom, $C_{1-2}$alkoxy optionally fluorinated, or $NR^1R^2$ where $R^1$ and $R^2$ independently are $C_{1-2}$alkyl or H;

the process comprising the steps of:

(i) optionally reducing a compound of formula (I):

(I)

wherein $P_1$ and $P_2$ are amino protecting groups as defined in any of claims 1 to 7, to a compound of formula (VII):

(VII)

wherein $P_1$ and $P_2$ are as defined in formula (I), in the presence of a first organic solvent;

(ii) reacting the compound of formula (VII) with a compound of formula (VIa):

R—ONH$_2$ (VIa)

or an acid addition salt thereof, wherein R is as defined in formula (IVa), in the presence of a second organic solvent, to form a compound of formula (VIIIa):

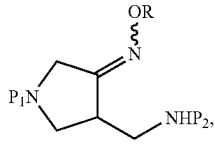

(VIIIa)

wherein $P_1$ and $P_2$ are as defined in formula (I) and R is as defined in formula (IVa); followed by (iii) removing the amino protecting groups $P_1$ and $P_2$ of the compound of formula (VIIIa) in the presence of a third organic solvent and a deprotecting agent capable of performing this removal, to form the compound of formula (IVa) or the salt thereof;

characterised in that, after formation of the compound of formula (VIIIa) in step (ii), part or all of the second organic solvent is removed and replaced by the third organic solvent without isolation of the compound of formula (VIIIa).

Preferred aspects of the above are as for the third aspect of the invention; with all necessary changes being made. For example, preferred aspects involving the compounds of formula (IV), (VI), (VIII) also apply to the compounds of formula (IVa), (VIa), (VIIIa) respectively. Preferably, R is $C_{1-6}$ alkyl optionally fluorinated (e.g. methyl, ethyl, n- or iso-propyl, n- s- iso- or t-butyl, trifluoromethyl, etc); $C_{2-4}$alkenyl (e.g. allyl); $C_{3-8}$ cycloalkyl with a 3–6-membered carbocyclic ring (e.g. cyclopropyl, cyclobutyl, cyclopentyl, cyclohexyl, methylcyclohexyl-, cyclohexylmethyl-, etc); or phenyl, naphthyl, benzyl or phenylethyl in which the aryl moiety is optionally substituted by one or two of methyl, ethyl, trifluoromethyl, F, Cl, Br, I, methoxy, trifluoromethoxy or $NMe_2$.

Compounds of formula (VIa), R—O—$NH_2$ or acid addition salts thereof, are either commercially available like methoxylamine or can be made using processes known to the skilled person. For example, R—O—$NH_2$ can be made from reaction of $NH_2$—OH or Protected —NH—OH or a salt with R—X where X is a leaving group such as R-Hal (Hal=halogen atom such as chloro) in the presence of a base where R is such that the halide is displaceable by a nucleophile. E.g. for m-CF3—C6H4—CH(Me)-O—$NH_2$ from the chloro derivative and AcNH—OK followed by deprotection see K. Tanaka et al., *J. Org. Chem.*, 2000, 65, 432–437 especially Scheme 4 and compound (2) synthesis on p.436. According to EP 0 678 504 A1, especially examples 13–36, R—O—$NH_2$ (e.g. wherein R=methyl, ethyl, n- or iso-propyl, n-butyl, allyl, 4-chlorobenzyl etc) can been made from reacting e.g. hydroxylamine sulfate with an ester such as EtOAc with 50% aqueous NaOH to form a hydroxamic acid AcNH—OH, O-alkylation of that with the sulphate $R_2SO_4$ or R—Cl or R—I, and acid hydrolysis. Where R=aryl such as optionally substituted phenyl, R—O—$NH_2$ can still be made: the R—OH phenolic-type compound can reacted in the presence of base with X—$NH_2$ where X=a leaving group such as (a) mesityl-$SO_2$—O— (e.g. *J. Med. Chem.*, 1989, 32, 1098), (b) $Ph_2$PON— (JP 200-108-1071, published 27 Mar. 2001), or (c) —OSO $_2$OH (e.g. JP 04368360, published 21 Dec. 1992); for 2,4,6-trimethoxyphenyl-O—NH2, see also *Synthesis*, 1980, 461.

A fourth aspect of the invention provides a process for the production of a compound of formula (VIII):

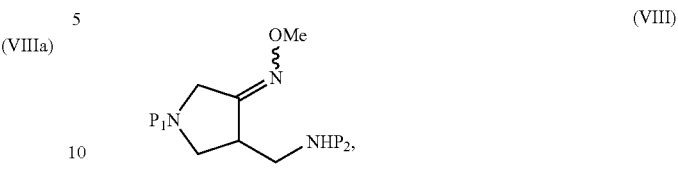

(VIII)

wherein $P_1$ and $P_2$ are amino protecting groups as defined herein, comprising the steps of:

(i) reducing a compound of formula (I):

(I)

wherein $P_1$ and $P_2$ are as defined in formula (VIII), to a compound of formula (VI):

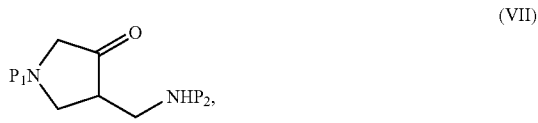

(VII)

wherein $P_1$ and $P_2$ are as defined in formula (VIII), in the presence of a first organic solvent; and (ii) reacting the compound of formula (VI) with a compound of formula (VI):

Me-$ONH_2$ (VI)

or an acid addition salt thereof (e.g. the HCl salt, Me-$ONH_2$.HCl) in the presence of a second organic solvent, to form a compound of formula (VIII);

characterised in that steps (i) and (ii) are carried out without isolation of the compound of formula (VII).

"Without isolation" is as defined above. As discussed above, this helps to increases the ease of the reaction, decreases the total time spent to convert of (I) to (VIII) e.g. on large scale, and therefore increases throughput compared to the WO 99/44991 A1 and WO 01/17961 A2 examples.

Preferable features of the fourth aspect of the invention (e.g. steps (i) and/or (ii) of the process, e.g. the first and/or second organic solvent) are as defined for the third aspect of the invention, any necessary changes having been made. For example, preferably the second organic solvent is or includes some or all of the first organic solvent. Preferably, the first organic solvent is a substantially water-immiscible organic solvent which does not consist essentially of dichloromethane or optionally chloroform. Preferably, the first organic solvent comprises, consists essentially of or is ethyl acetate; the first solvent can suitably include or be toluene, xylene, and/or t-butyl methyl ether. The first organic solvent is preferably as defined herein for the second organic solvent in step (ii), independent of the second organic solvent.

Similarly, the fourth aspect of the invention also more generally provides a process for the production of a compound of formula (VIIIa):

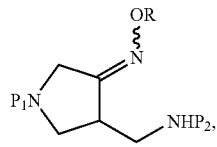
(VIIIa)

wherein $P_1$ and $P_2$ are amino protecting groups as defined herein, and wherein R is $C_{1-10}$ alkyl optionally fluorinated; $C_{2-6}$alkenyl; $C_{3-10}$ cycloalkyl with a 3–8-membered carbocyclic ring; $C_{6-14}$aryl; $C_{2-13}$ monocyclic, bicyclic or tricyclic heteroaryl; or $C_{6-14}$aryl $C_{1-4}$alkyl; wherein any aryl or heteroaryl moieties are optionally substituted by one, two or three of: $C_{1-3}$ alkyl optionally fluorinated, a halogen atom, $C_{1-2}$alkoxy optionally fluorinated, or $NR^1R^2$ where $R^1$ and $R^2$ independently are $C_{1-2}$alkyl or H;

the process comprising the steps of:

(i) reducing a compound of formula (I):

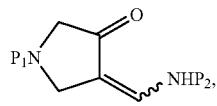
(I)

wherein $P_1$ and $P_2$ are as defined in formula (VIIIa), to a compound of formula (VII):

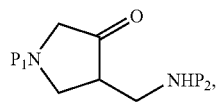
(VII)

wherein $P_1$ and $P_2$ are as defined in formula (VIIIa), in the presence of a first organic solvent; and (ii) reacting the compound of formula (VID with a compound of formula (VI):

R—ONH$_2$ (VIa)

or an acid addition salt thereof (e.g. the HCl salt, R—ONH$_2$.HCl), wherein R is as defined in formula (VIIIa), in the presence of a second organic solvent, to form a compound of formula (VIIIa);

characterised in that steps (i) and (ii) are carried out without isolation of the compound of formula (VII).

A fifth aspect of the invention provides a process for the production of a compound of formula (III), or a pharmaceutically acceptable salt and/or hydrate thereof:

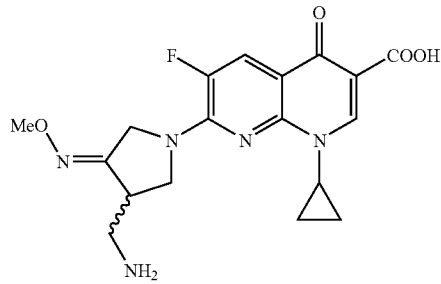
(III)

which comprises:

(1) optionally producing a compound of formula (I) as defined herein according to a process described in the first aspect of the invention; and (2) converting a compound of formula (I) as defined herein to a compound of formula (IV):

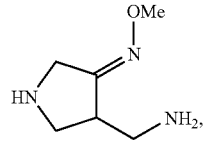
(IV)

or a salt thereof, according to the third aspect of the invention; and/or converting a compound of formula (I) as defined herein to a compound of formula (VIII):

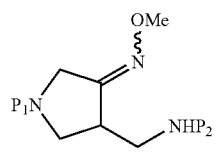
(VIII)

according to the fourth aspect of the invention and then converting the compound of formula (VIII) to a compound of formula (IV); followed by (3) reaction of the compound of formula (IV) or the salt thereof, with a compound of formula (V):

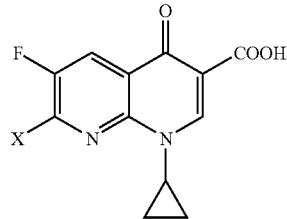
(V)

wherein X is a leaving group; and (4) optionally forming a pharmaceutically acceptable salt and/or hydrate thereof.

A further aspect of the invention provides a compound of formula (III), or a pharmaceutically acceptable salt and/or hydrate thereof, (a) obtainable by, or (b) which has been (whenever) obtained (produced) by, a process according to the fifth aspect of the invention.

All publications, including but not limited to patents and patent applications, cited in this specification are herein incorporated by reference as if each individual publication were specifically and individually indicated to be incorporated by reference herein as though fully set forth.

EXAMPLES

The invention is illustrated by the following examples. However, it should be understood that the Examples are intended to illustrate but not in any manner limit the scope of the invention. Some of the Examples are described with reference to the FIGS., in which:

Example 1

Process Example Using Intensified Plug Flow Reactor

Figure 1:
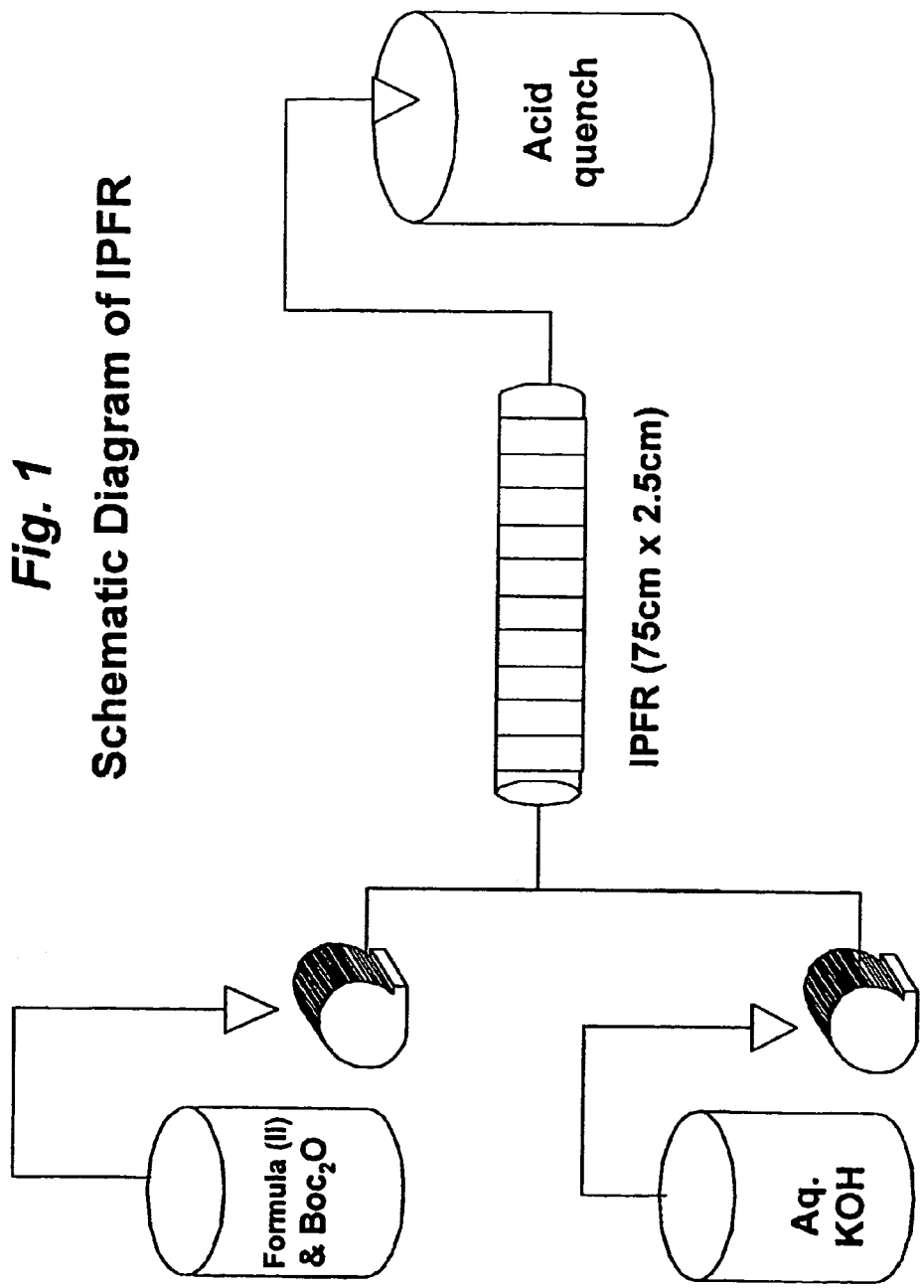
FIG. 1 is a schematic diagram of an Intensified Plug Flow Reactor (IPFR) as used in Example 1.

An Intensified Plug Flow Reactor (IPFR) was used to conduct a series of experiments in which parameters known to have an influence on reaction selectivity, such as temperature, flow rate and stoichiometry were evaluated. Referring to FIG. 1, the IPFR was composed of:
- 2 jacketed glass kettles (5 L and 10 L) as feed tanks
- 2 Micropumps (max flow 120 ml/min and 240 mL/min)
- 1 jacketed SS316 tube filled with Sulzer SMV mixing elements: 75 cm long*2.5 cm bore diameter
- 15 L product collection tank
- Temperature probes, pressure gauges, pressure relief valve, nitrogen purging, insulated lines A solution of 1-(N-t-butoxycarbonyl)-4-aminomethylene-pyrrolidin-3-one in aqueous isopropanol (e.g. 5:1 v/v isopropanol:water) was mixed with t-butoxycarbonyl anhydride (e.g. 1.2 equivalents) and was stored in a 10 L vessel under a nitrogen blanket. A solution of 30% W/W potassium hydroxide in water was stored in a 5 L vessel. Both tanks were cooled down to −5° C. Both streams were fed in the jacketed static mixer cooled down to −20° C. The reacted mixture obtained was then quenched into a stirred collection tank containing acetic acid, demineralised water and isopropanol (IPA) (e.g. 2:1:1 acetic acid:water: IPA by volume). Samples were taken for each new set of parameters when steady state was reached and residual 1-(N-t-butoxycarbonyl)-4-aminomethylene-pyrrolidin-3-one measured by HPLC. Temperature was also recorded over the length of the static mixer.

Table 1 below compares the HPLC results obtained for impurity profiles in the batch-mode reaction and in the IPFR static mixer for the by-products created:

TABLE 1 impurity profiles

| Compound | IPFR Static mixer [% HPLC area] | Batch mode [% HPLC area] |
|---|---|---|
| Isomer | 6.2 | 3.1 |
| Dimers | 0.09 | 0.8 |

The isomer (of the compound of formula (I)) is consumed in the next hydrogenation stage. The dimers created in the batch-mode reaction reduce the crystallisation yield and are due to inadequate temperature control in the batch-mode reaction.

A summary of some of the results are given in Table 2 below. The best conversion using the IPFR equipment is attained at modest flow rates and low temperature.

TABLE 2

Experimental Results for the Intensified Plug Flow Reactor

| Residence time (mins) | Formula (II) flow rate (mL/min) | aqueous KOH flow rate (mL/min) | Jacket temperature (° C.) | % Conversion |
|---|---|---|---|---|
| 4.8 | 48 | 24 | −20 | 94.5 |
| 13 | 18 | 9 | −23 | 96 |
| 13 | 18 | 9 | −15 | 92.2 |

In an optional variation of Example I above, the outlet temperature was also measured for each of the above three test results and was found to be −1.3, −11.1 and −3.2° C. respectively (i.e. for the above tests using jacket temperatures of −20, −23 and −15° C. respectively). The empty pipe Reynolds numbers for these 3 optional experiments were 60, 23, 23 respectively.

It can be seen from Table 2 that the highest conversion was reached at a low flow rate and a low temperature. Also, in a variation of Example 1, it was found that as the temperature rises impurities were observed to appear (or impurity levels increased) and conversion decreased. In another variation of Example 1, a higher flow rate of aqueous KOH was investigated but this gave decreased conversion.

Figure 2:
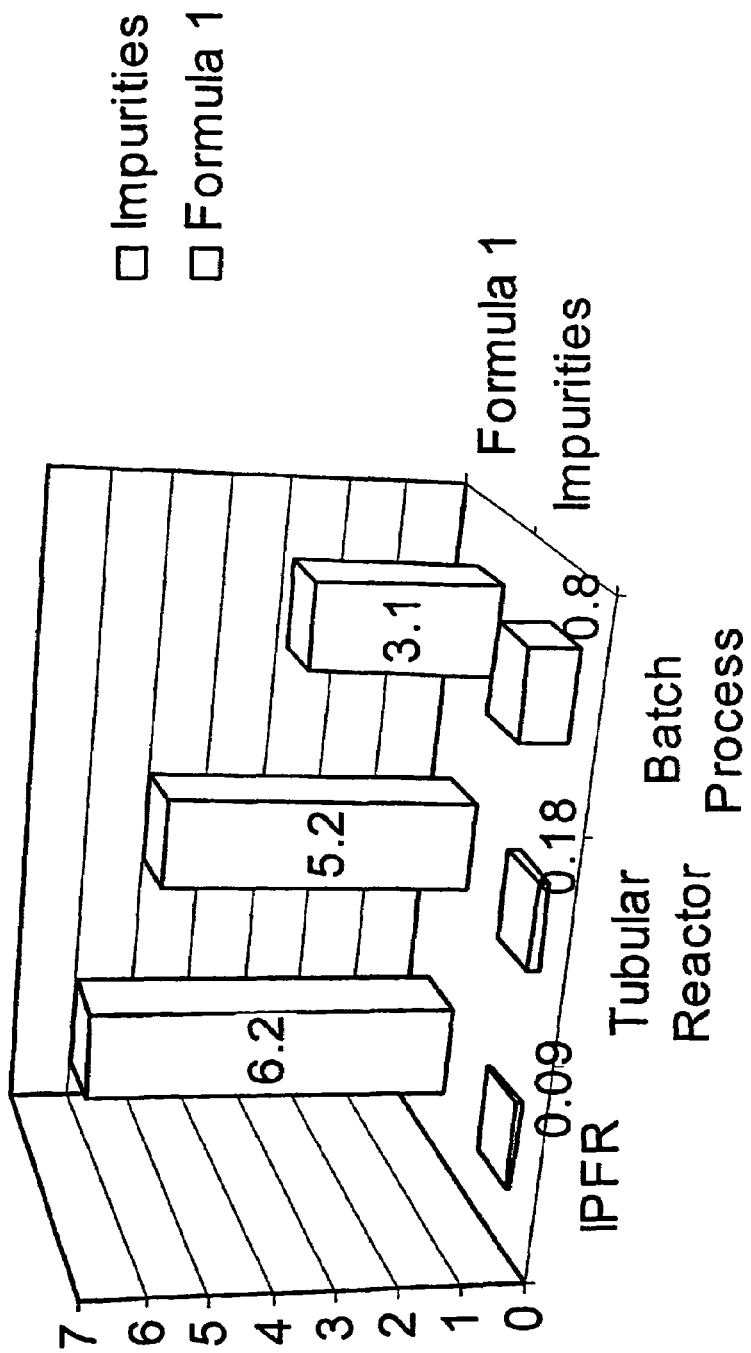
FIG. 2 is a bar graph showing a comparison of results obtained using (a) the IPFR according to Example 1, (b) the tubular reactor according to Example 5, and (c) the known batch process for the production of 1-(N-t-butoxycarbonyl)-4-(N-t-butoxycarbonyl)aminomethylene-pyrrolidin-3-one.

Referring again to Example 1, the main advantage of operating this process in continuous mode is the reduction of dimer impurity levels in the reacted mixture by one order of magnitude compared to the batch-mode reaction. These impurities are known to rise with extended exposure to the alkaline reaction mixture and increased reaction temperature. On occasion they have even reached levels in prepared batches where crystallisation of the product has been hindered. These adverse conditions can be avoided or mitigated in continuous mode, which features superior control over degree of mixing, uniformity of bulk temperature and reaction mixture residence time. FIG. 2 compares quantities of by-products obtained for the two operating modes: batch and continuous.

Example 2

Process Examples Using a Series of Kenics® Static Mixers

Figure 3:
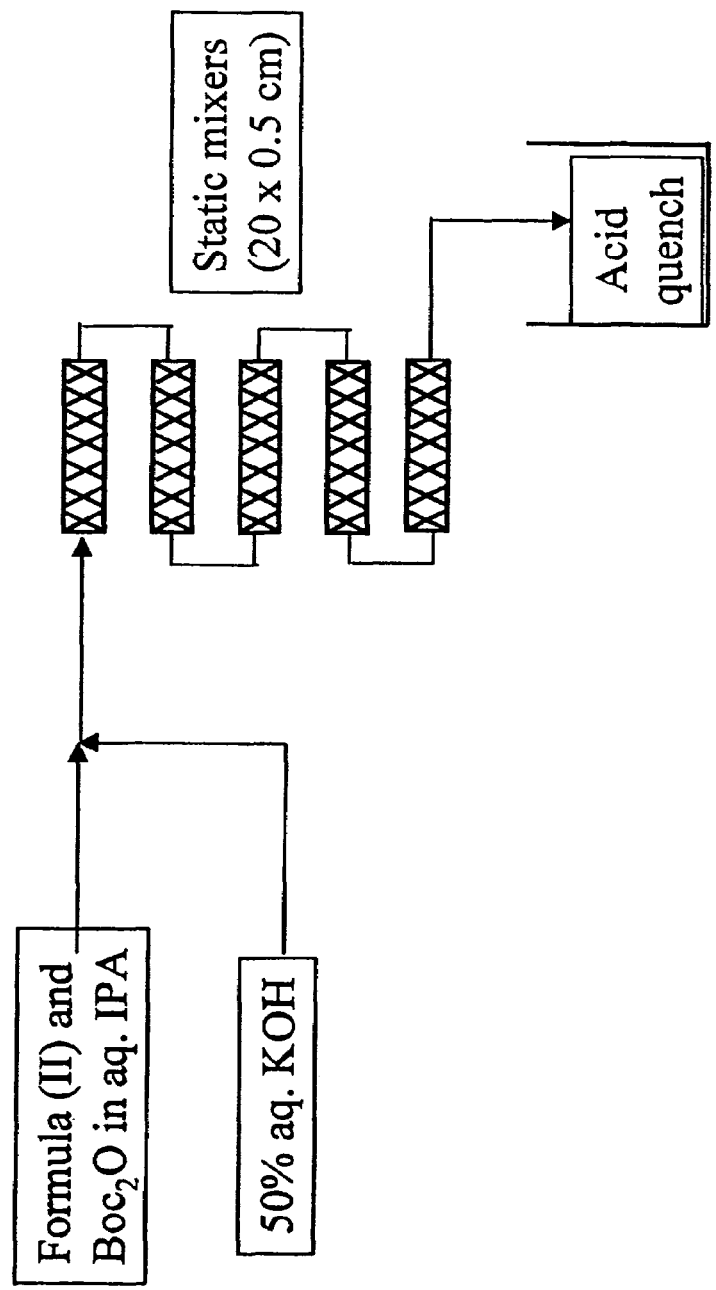
FIG. 3 is a schematic diagram of laboratory line static mixers as used in Examples 2–4.

With reference to FIG. 3, using a series of Kenics® Static mixers (length 20 cm, od 0.5 cm, id 0.33 cm), in particular Kenics® KM Static mixers, with the outlet passing into an acid quench, it was established that using an excess of base virtually quantitative conversions could be obtained, see Tables 3 and 4 below. Experiments also demonstrated that with high flow rates a lower residence time was required, or significant decomposition products were formed. From the initial work a further set of experiments was undertaken to obtain a better understanding of the correlation of residence time and conversion, and for this work six equivalents of 50% KOH were used. Under the reaction conditions of excess base, conversions >97% could be obtained with very short retention times, see table 5. Typically in this last series of experiments a combined flow rate of 60 mL/min was used and a residence time of 30 secs.

TABLE 3

Comparison of Conversion and Equivalents of Base

| Equivalents of | Conversion (%) | | | |
|---|---|---|---|---|
| 50% KOH | 1 min* | 2 min* | 3 min* | 4 min* |
| 12 | 98.2 | 98.4 | | 98.1 |
| 7 | 97.5 | 97.0 | 98.0 | 97.8 |
| 6 | 97.0 | 97.2 | 97.3 | |
| 5 | 95.8 | 96.1 | 96.0 | |

*Time elapsed from startup of operation

TABLE 4

Comparison of Conversion and Retention Time

| Retention time (secs) | Equivalents of 50% KOH | Conversion (%) | | |
|---|---|---|---|---|
| | | 1 min* | 2 min* | 3 min* |
| 10 | 6 | 97.5 | 97.1 | 97.4 |
| 20 | 6 | 96.0 | 97.0 | 97.0 |
| 30 | 6 | 97.0 | 97.2 | 97.3 |

*Time elapsed from startup of operation
*In one optional embodiment, samples were collected at 1 min, 2 min and 3 min and 4 min after starting the operation of the pump. The same level of conversion at each time of sampling shows that the induction period (or the time to reach the steady state) is very short.

In an alternative embodiment of Example 2, the above Example 2 processes were repeated using the apparatus shown in FIG. 3A and described in Example 3 below.

In another alternative embodiment of Example 2, some scale up work on this process has been undertaken and by using larger static mixers flow rates of 2 L/min have been achieved with similar conversion rates (this is exemplified in Example 4).

Example 3

Process Example Using Kenics® KM Static Mixers, and Apparatus Therefor

When Kenics® KM Static mixers (length 20 cm, od 0.5 cm, id 0.33 cm) were employed using the apparatus shown in FIG. 3A and described below, a solution of 1-(N-t-butoxycarbonyl)-4-aminomethylene-pyrrolidin-3-one in aqueous isopropanol mixed with 1.2 equivalents of t-butoxycarbonyl anhydride was prepared in a vessel with a nitrogen blanket. It was mixed with a solution of 4 to 15 equivalents of 50% w/w potassium hydroxide in water. A solution of 6 to 10 equivalents, most preferably 6 equivalents, of 50% w/w potassium hydroxide in water was more preferred. Both feed streams were cooled down to 0° C. and the coolant temperature around the Kenics KM static mixer was set to 0° C. When a flow rate of 120 mL/min with a residence time of 5 sec was used, the conversion >96% was achieved.

Figure 3A:
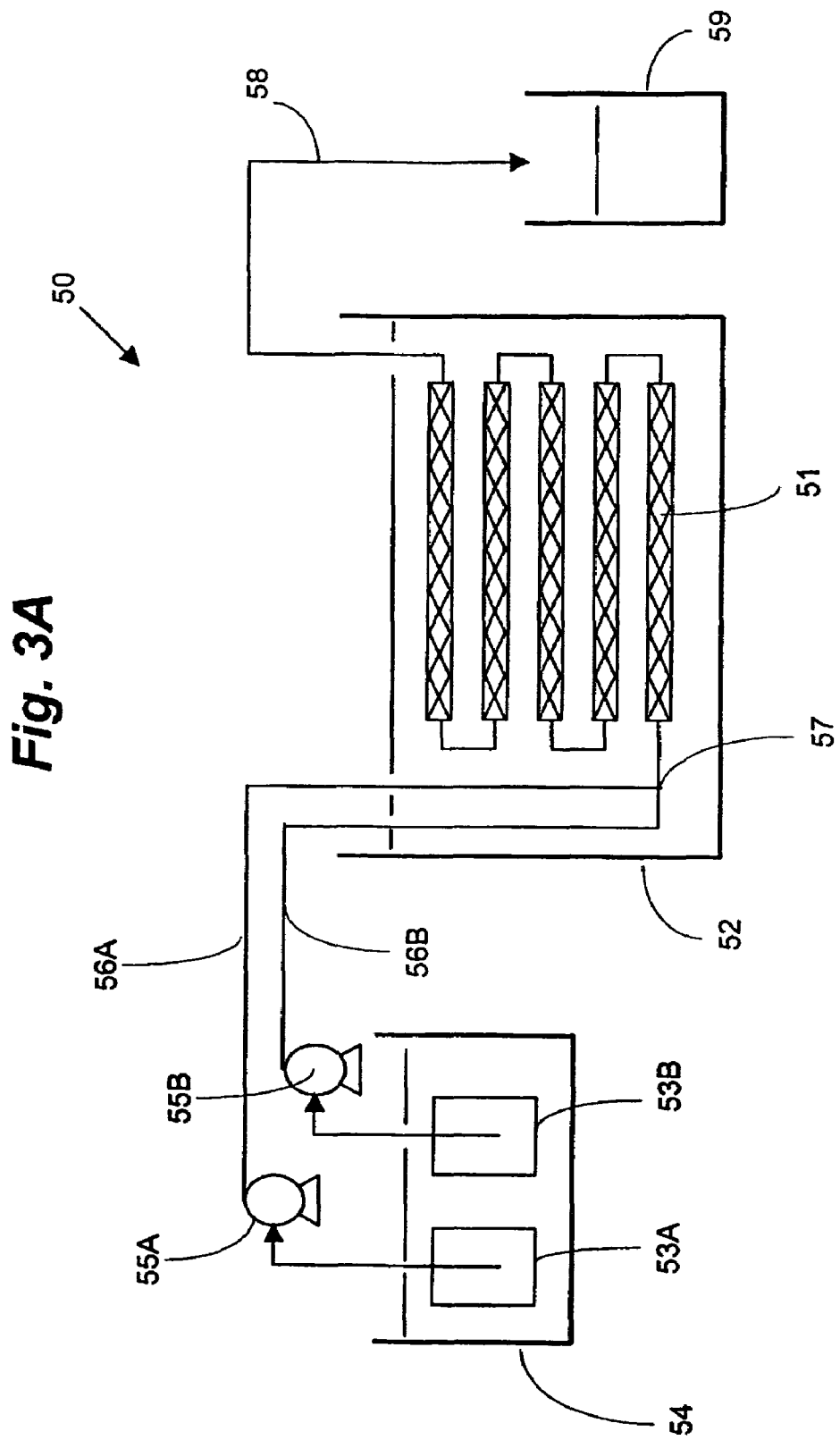
FIG. 3A is a schematic diagram of a laboratory apparatus comprising five static mixers in series, as described and used in Example 3.

The laboratory apparatus 50 used in the above Example 3 process is shown as a schematic diagram in FIG. 3A. The apparatus 50 employs five separate static mixers 51, each comprising a tubular reactor (length 20 cm, outside diameter od=0.5 cm, inside diameter id=0.33 cm) containing twenty-seven "Kenics KM-type" static mixing elements which are as described in Example 8 below. The material of contruction of the static mixers 51 (both the tubular housing and the mixing elements) is SS316, a well-known Fe—Ni—Cr—Mo alloy. The five static mixers 51 are arranged in series in fluid communication with each other and all mixers are submerged in a first temperature-controlled coolant bath 52.

Two sealed feed tanks 53A, 53B submerged in a second temperature-controlled coolant bath 54 contain the two reagent solutions, namely:

tank 53A: a solution of 50% w/w potassium hydroxide in water; and tank 53B: a solution of 1-(N-t-butoxycarbonyl)-4-aminomethylene-pyrrolidin-3-one in aqueous isopropanol mixed with 1.2 equivalents of t-butoxycarbonyl anhydride; tank 53B has a nitrogen blanket.

The reagent solutions can be pumped out of the tanks 53A, 53B via pumps 55A, 55B into pipes 56A, 56B which enter the first coolant bath 52 and then become joined in a simple T-piece 57 made of SS316 Fe—Ni—Cr—Mo alloy. After mixing of the reagent streams the mixture enters the first of the five mixers 51. The distance between the T-piece 57 and the first mixer 51 is as short as possible. Downstream of the five mixers 51, an reacted mixture pipe 58 is fed into an open-topped receiving vessel 59 containing the acid to quench the reaction.

In Example 3, the first and second coolant baths 52 and 54 are both ice baths maintained at 0° C. However, in alternative embodiments, other suitable cooling media such as ethylene glycol can be used e.g. to achieve lower temperatures. Temperatures of −15° C. can be achieved using ethylene glycol coolant.

Example 4

Large-Scale Process Example Using a Kenics® Static Mixer

The Kenics KM static mixer having outside diameter of 1.3 cm and internal diameter of 1.09 cm was used with a flow rate of 1 L/min and the residence time was 15 sec. A solution of 10 equivalents of 50% w/w potassium hydroxide in water was used. When both feed streams were cooled down to 0° C. and the coolant temperature around the Kenics KM static mixer was set to 0° C., the conversion >96% was achieved.

Example 5

Initial Pilot Scale Experiments

Figure 4:
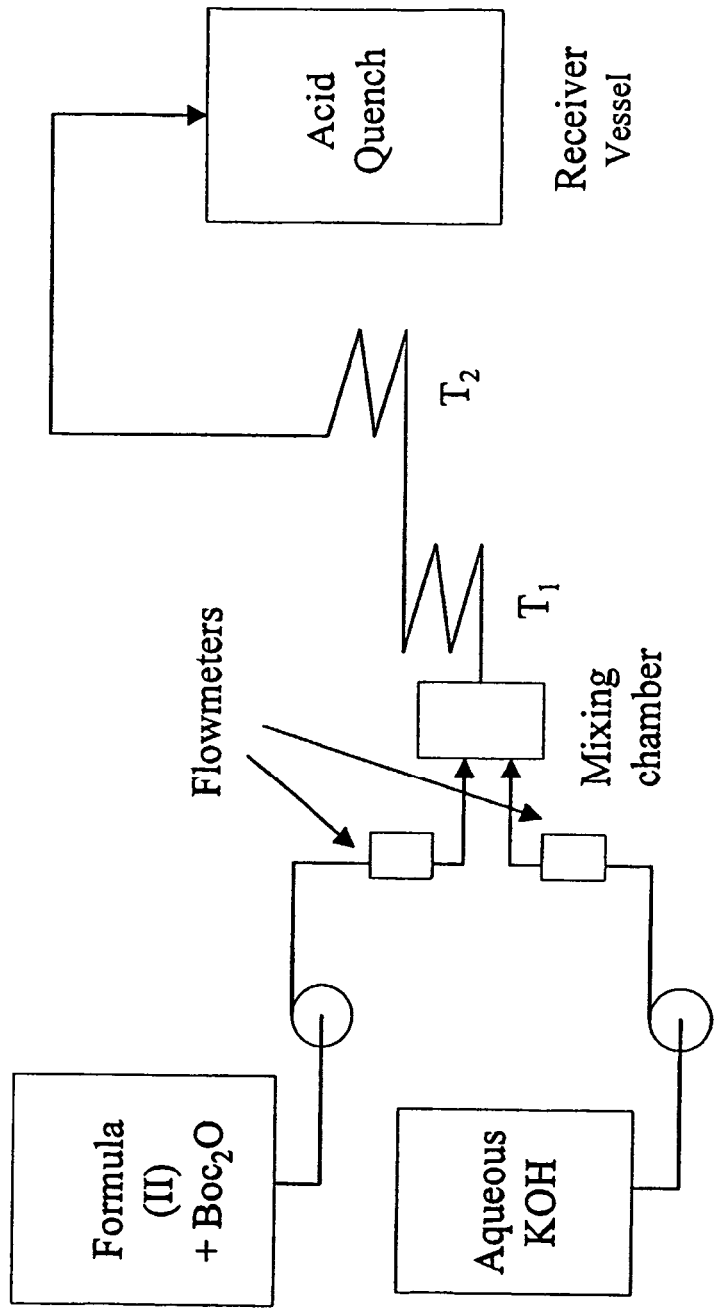
FIG. 4 is a schematic diagram of pilot scale equipment as used in Example 5.

For the initial pilot scale experiments a combination approach involving rapid stream mixing and a two-stage tubular reactor was used, shown schematically in FIG. 4. As with the laboratory experiments, the 1-(N-t-butoxycarbonyl)-4-aminomethylene-pyrrolidin-3-one/t-butoxycarbonyl anhydride stream (e.g. a solution of these 2 ingredients in 5:1 v/v isopropanol:water, e.g. using 1.2 equivalents of t-butoxycarbonyl anhydride) was mixed with a caustic aqueous potassium hydroxide stream (e.g. 22.5% w/w potassium hydroxide solution, 4 equivalents). The reaction mixture was passed through a mixing chamber and into the tubular reactor (two 7.5 m×10 mm pipes $T_1$ and $T_2$) situated in a cool bath maintained at −5 to −15° C. The outflow was quenched into acetic acid (or in an alternative embodiment, quenched into a mixture of acetic acid, water and isopropanol 2:1:1 by volume). The protected enaminoketone, 1-(N-t-butoxycarbonyl)-4-(N-t-butoxycarbonyl)aminomethylene-pyrrolidin-3-one was isolated by heating the quenched mixture to 35 to 40° C. thus creating two layers. The bottom aqueous layer was separated off and discarded. An equivalent volume of deionised water was added to the remaining isopropanol solution from which the 1-(N-t-butoxycarbonyl)-4-(N-t-butoxycarbonyl)aminomethylene-pyrrolidin-3-one crystallised.

Conversion rates were good, typically >90% or >95%. At low flow rates and low temperatures extremely high conversions of starting material to product were obtained. A stock of 1-(N-t-butoxycarbonyl)-4-aminomethylene-pyrrolidin-3-one was generated and the pilot rig was run for about 10 hours, producing 1-(N-t-butoxycarbonyl)-4-(N-t-butoxycarbonyl)aminomethylene-pyrrolidin-3-one suitable for onward processing. Based on this work and other plant experiments calculations have confirmed that production targets in excess of 500 kg per week could be obtained by using this tubular equipment and with minor modifications to the current rig the output could be increased to 1–1.5 tonnes per week.

In an optional variation of Example 5, the two reactor pipes $T_1$ and $T_2$ are coiled stainless steel tubes, the coolant baths for the two tubes contain glycol, the first tube $T_1$ is in a bath cooled to −15° C. to remove the heat of the reaction, and the second tube $T_2$ is in a bath cooled to −5° C. to maintain the desired reaction temperature.

In another optional variation of Example 5, the empty pipe Reynolds number was 1350, and the following other reaction parameters were used:

| Residence time (mins) | Formula (II) solution flow rate (mL/min) | aqueous KOH flow rate (mL/min) | Jacket temperature (° C.) | % Conversion |
|---|---|---|---|---|
| 4.9 | 150 | 90 | −15 and −5 | 93.5 |

Another variation of Example 5 involves the replacement of the two reactor pipes $T_1$ and $T_2$ with a single coiled stainless steel reactor tube submerged in a glycol coolant bath, and replacement of the mixing chamber with a 3-way stainless steel T-piece low dead-volume connector. The T-piece mixes the two reagent fluid streams and the resultant mixed stream passes to the cooled reactor tube.

Example 6

Intensified Plug Flow Reactor (IPFR) Apparatus Description, and Process

Figure 5:
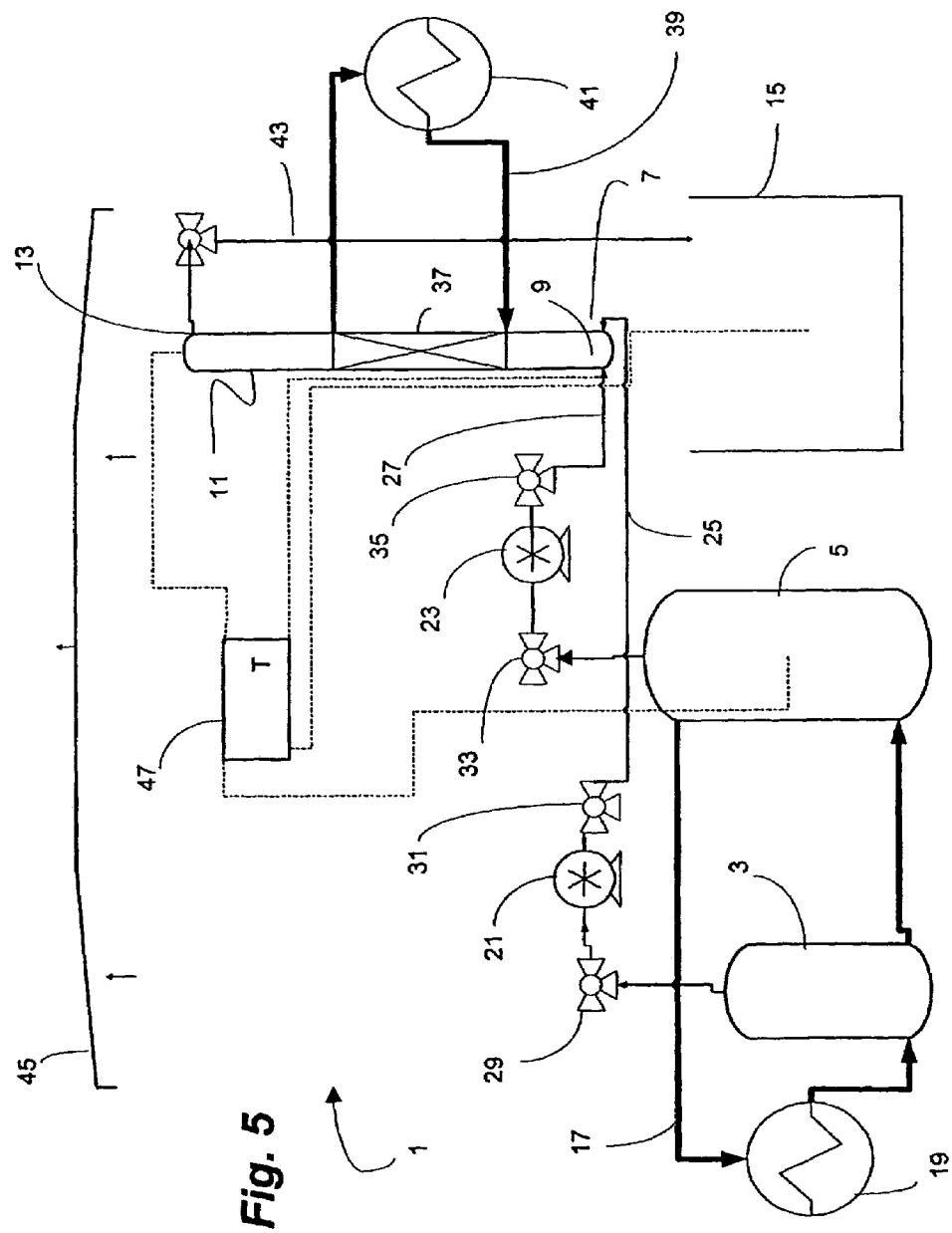
FIG. 5 is a detailed schematic diagram of the Intensified Plug Flow Reactor (IPFR) described in Example 6.

FIG. 5 shows a schematic diagram of an Intensified Plug Flow Reactor (IPFR) apparatus, in more detail than the IPFR shown in FIG. 1. The FIG. 5 apparatus can optionally be used as the IPFR plug flow reactor in the continuous processing mode reaction of the first aspect of the invention described in Example 1.

Referring to FIG. 5, the apparatus 1 for use in the continuous processing mode reaction comprises first and second jacketed feed tanks 3, 5 containing two separate reagent solutions, the feed tanks 3, 5 being in fluid communication with a tubular plug flow reactor 11 (IPFR) respectively via inlet ports 7, 9 which are at or adjacent one end of the reactor 11. The reactor 11 is adapted to continually mix and split the two input reagent streams as they pass therealong. An outlet port 13 at or adjacent the opposing (downstream) end of the reactor 11 allows the reaction stream(s) to flow out from the reactor and into an open-topped receiver tank 15.

The jackets of the reagent feed tanks 3, 5 are hollow and are in fluid communication with a circular heat exchanger circuit 17 adapted to contain a heat transfer fluid in which circuit the tanks 3, 5 and a Lauda heat exchanger 19 are connected in series. This allows the feed tanks to be cooled or heated as desired.

The two pre-heated or pre-cooled streams containing reagents for the reaction can be fed from the two jacketed feed tanks 3, 5 via two separately controlled gear pumps 21, 23 and feed lines 25, 27 into the tubular reactor 11. These Micropumps 21, 23 are controlled by inverters, allowing a combined total flow range of from 30 to 400 mL.min$^{-1}$. Both pump outlets are fitted with pressure gauges and non-return valves 29, 33 to ensure that over-pressurisation and back flow do not occur in the feed lines.

As for the tubular reactor 11, two versions were built: one made of glass for initial observation and demonstration purposes and one made of SS316 alloy (a well-known Fe—Ni—Cr—Mo alloy) to carry out reactions.

Whichever reactor is used, the tubular reactor 11 is fitted vertically as shown in FIG. 5, and has an internal diameter of 25.4 mm and a length of 750 mm, creating a total liquid hold-up volume of 350 mL.

The reactor 11 can be fitted with precision diameter Halar ETFE Sulzer® SMV mixing elements, for example as described in Example 7. Halar ETFE is chosen as material of construction for the mixing elements as it offers good resistance to most chemicals commonly encountered in pharmaceuticals processes. The "Sulzer® SMV-type" geometry of the mixing elements is selected on considerations regarding versatility. These mixing elements can handle low viscosity solvents but also gas/liquid systems and immiscible liquids of medium viscosity without generating excessive pressure drop which might affect the pumps 21, 23.

The reactor 11 is provided with a jacket 37 over the whole length of the reactor 11, the jacket 37 being in fluid communication via line 39 with a Huber CC231® heat exchanger 41. In use, the reactor 11 is heated or cooled by a heat transfer fluid (silicone oil) flowing through the jacket body 37. Using the silicone oil with the Huber CC23® heat transfer unit allows a wide temperature range for the experiments, from −30 to 250° C.

The receiver tank 15 is also jacketed to allow quenching of the reacted stream 43, if necessary.

All equipment is suitably earthed and fitted within a metal framework in a walk-in fume cupboard 45. Sampling points are installed at the pumps outlets and at the reactor inlets 7, 9 and outlet 13.

Three K type thermocouples are fitted in the reactor: at or near the mixing point of the two inlet streams 7, 9, at mid-length of the reactor (not shown) and at or near the outlet of the reactor 13. These thermocouples are connected to a digital thermometer 47 via lines some of which are shown as dot-dash lines in FIG. 5.

To prevent over-pressurisation of the set-up in the event of line or reactor blockage, a pressure relief valve is fitted on the reactor 11 and two additional pressure relief valves 31, 35 are fitted immediately after the pumps 21, 23 and linked to a recirculation loop (not shown) to the feed tanks 3, 5.

In use, in an embodiment of the process of Example 1, the first feed tank 3 has a 5 litre capacity and contains the 30% w/w aqueous potassium hydroxide solution; and the second feed tank 5 has a 10 litre capacity and contains the 1-(N-t-butoxycarbonyl)-4-aminomethylene-pyrrolidin-3-one of formula (H) and the $Boc_2O$ (e.g. 1.2 equivalents) in isopropanol/water (e.g. 5:1 v/v) under a nitrogen blanket. Both tanks 3, 5 are cooled down to −5° C. Both streams 25, 27 are fed into the jacketed static mixer 11 cooled down to −20° C. The reacted mixture obtained is then quenched into the 15-litre stirred collection tank 15 containing acetic acid, demineralised water and isopropanol (IPA) (e.g. 2:1:1 acetic acid:water: IPA by volume).

Example 7

"Sulzer® SMV-Type" Static Mixing Element and a Plug Flow Reactor Containing Such Mixing Elements FIGS. 6–9 show a "Sulzer® SMV-type" static mixing element which can be used in a plug flow reactor in the continuous mode process of the invention, especially with the apparatus/process of Examples 1 and 6.

Figure 6:
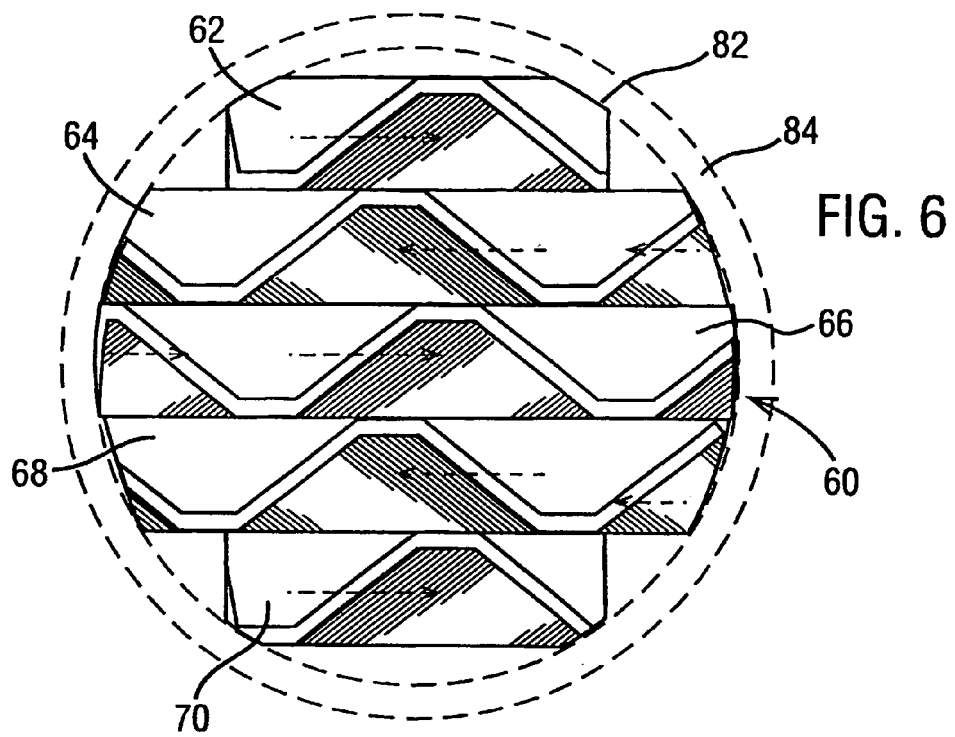
FIG. 6 is an end (axial) view of a "Sulzer SMV-type" static mixing element as described in the general description and Example 7.

FIGS. 6–9 illustrate a static mixing element 60 comprising a plurality of (here, five) stacked corrugated sheets 62, 64, 66, 68, 70, wherein the grooves 72, 72A, 74, 74A, 76, 78, 80 of each corrugated sheet are substantially perpendicular to the grooves of each directly adjacent corrugated sheet (i.e. the sheet directly above and the sheet directly below). "Stacked" in this context means "flat-stacked", i.e. with reference to the exploded top perspective view of FIG. 8 the grooves (e.g. 74, 74A) of the corrugated sheets (e.g. 64) are directed generally towards (i.e. generally face) the grooves (e.g. 72A, 76) of any directly adjacent corrugated sheet (e.g. 64, 66 respectively). In this mixing element 60, in use the plurality of stacked corrugated sheets splits and mixes the fluid stream width-wise across the sheets. As shown in FIG. 6, the mixing element is substantially cylindrical in outside profile 82, so as to fit snugly within an tubular reactor/ housing 84, with the cylinder axis being substantially parallel to the planes of the corrugated sheets 62-70.

In one optional variation, Halar ETFE is chosen as material of construction for the mixing elements 60 as it offers good resistance to most chemicals commonly encountered in pharmaceuticals processes.

Figure 7:
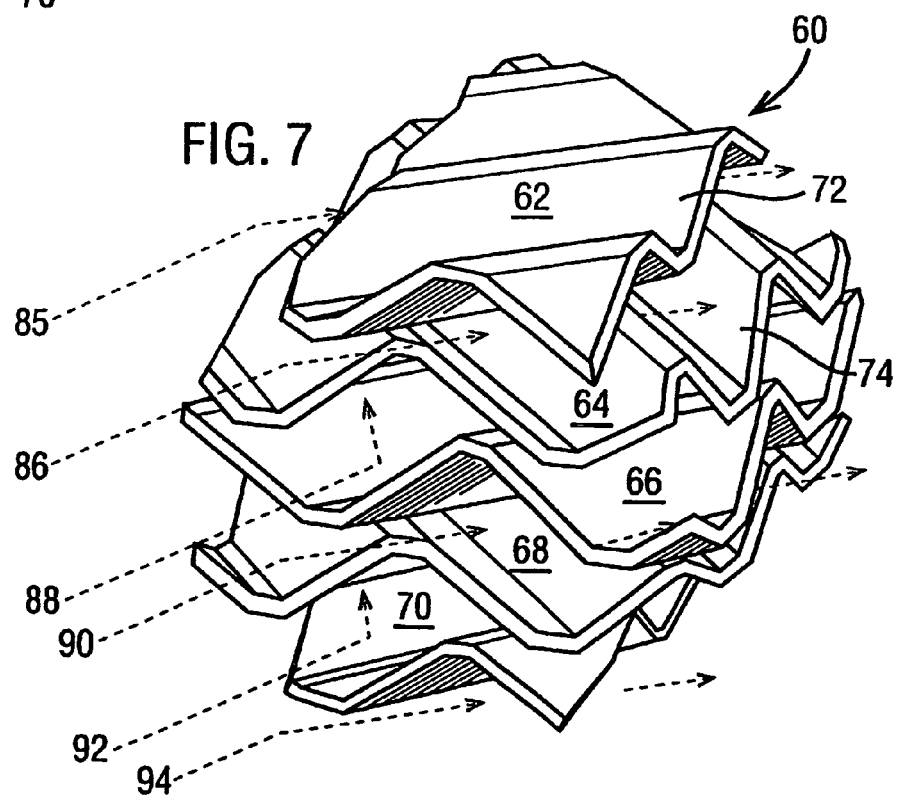
FIG. 7 is a top perspective view of the "Sulzer SMV-type" static mixing element shown in FIG. 6.
Figure 8:
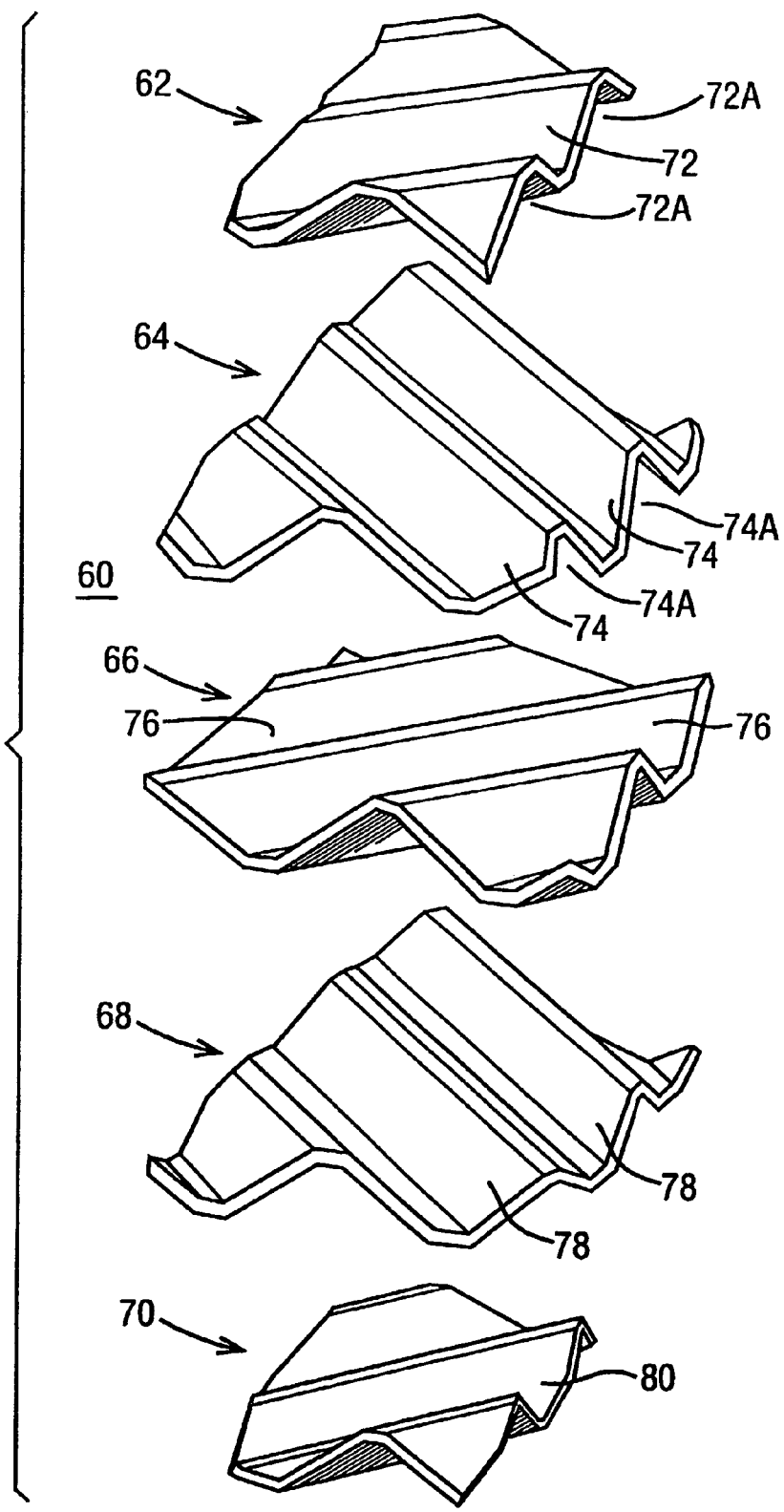
FIG. 8 is an exploded top perspective view of the "Sulzer SMV-type" static mixing element shown in FIGS. 6 and 7.
Figure 9:
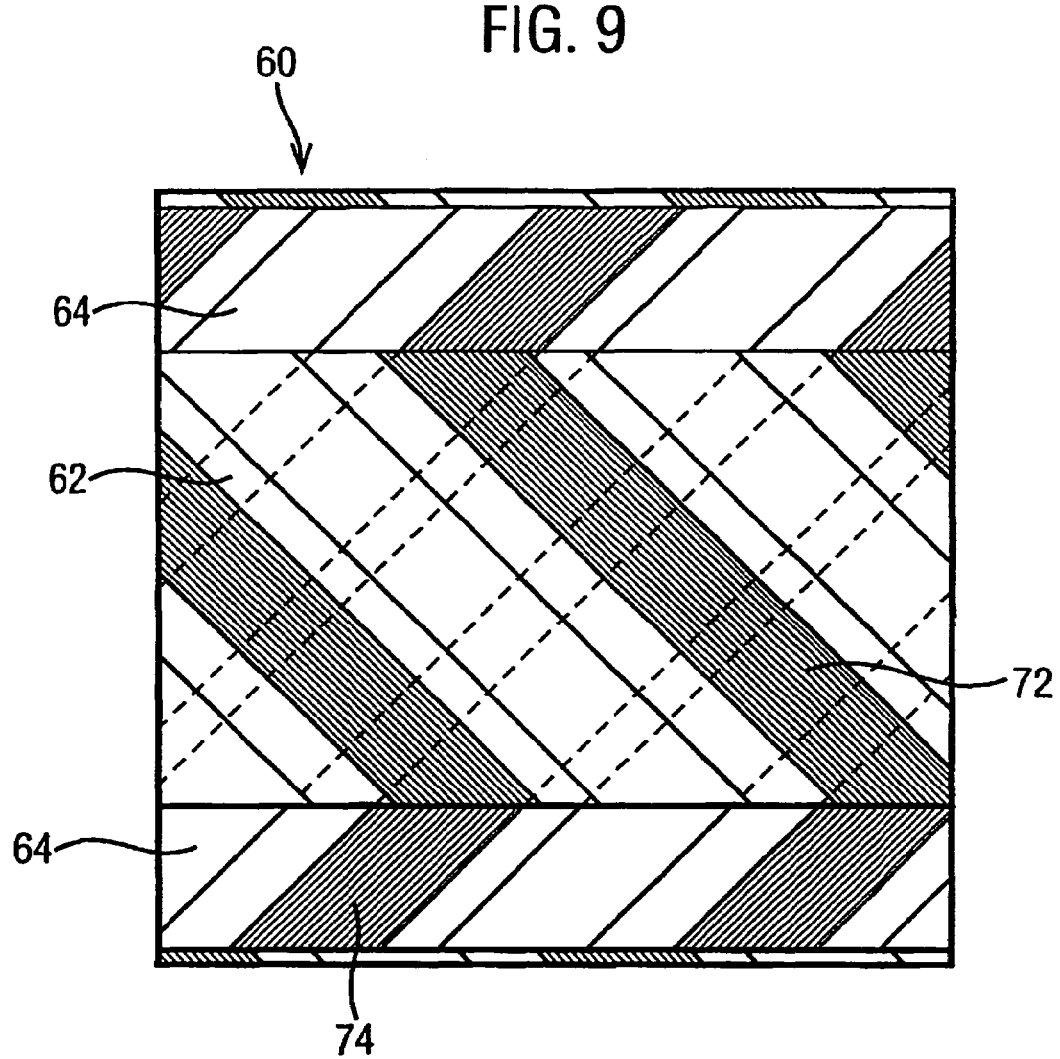
FIG. 9 is an top view of the "Sulzer SMV-type" static mixing element shown in FIGS. 6, 7 and 8.

As shown in FIG. 7, the mixing elements 60 when inside a pipe (e.g. a plug flow reactor) continually split and remix the reaction streams 85-94 promoting mass and heat transfer. Thus, even for low flow-rates and Reynolds numbers, a uniform plug flow profile with turbulent fluid flow can be achieved.

Figure 10:
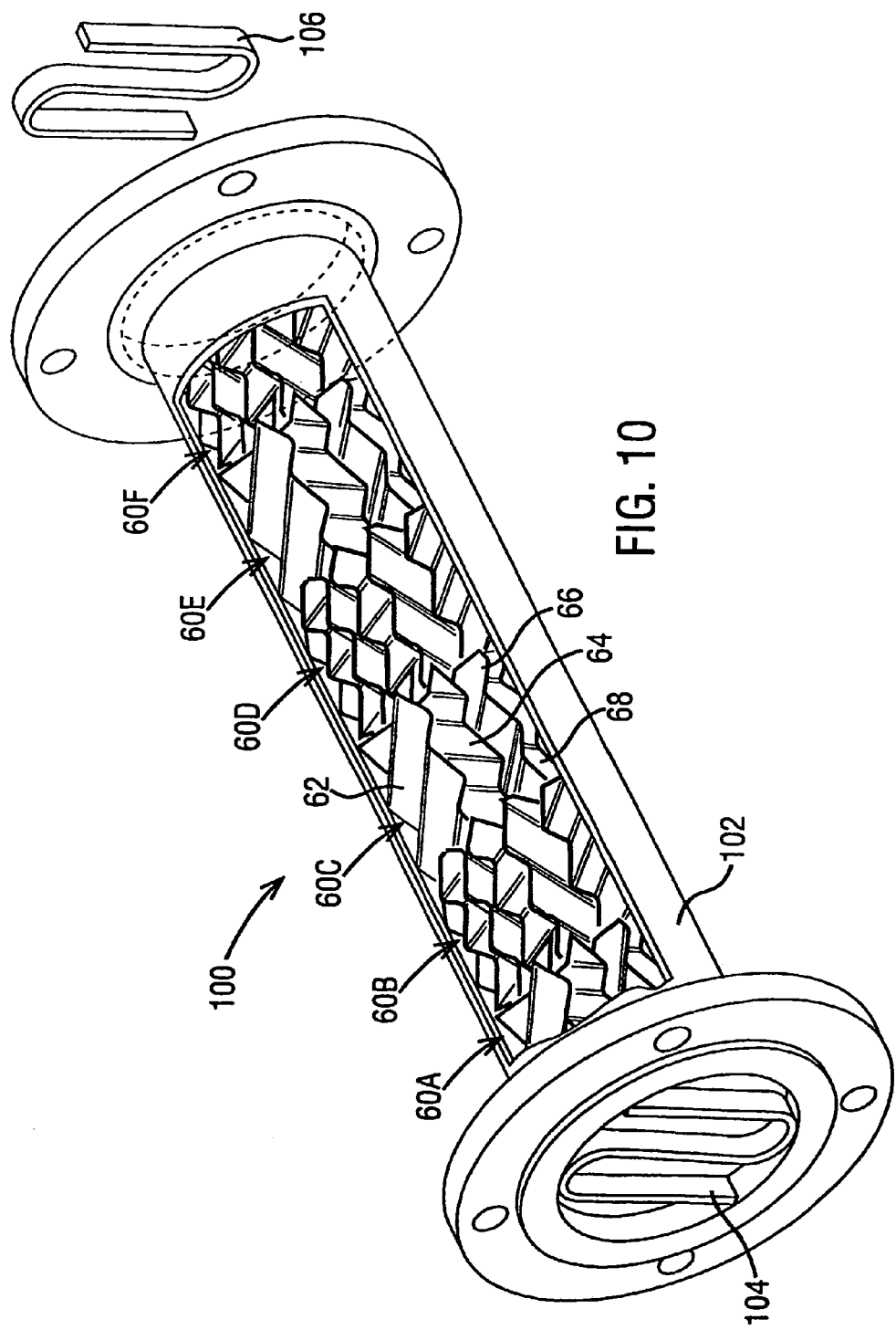
FIG. 10 is a cut-away top perspective view of the "Sulzer SMV-type" plug flow reactor containing a plurality of the static mixing elements shown in FIGS. 6–9 within a tubular housing/reactor, as described in the general description and Example 7.

As shown in FIG. 10, in the plug flow reactor 100, a plurality of the mixing elements 60 (here, six, designated 60A–F) are substantially axially aligned within an elongated tubular reactor (tubular housing) 102, with the corrugated sheets 62-68 arranged so as to allow fluid flow longitudinally along the tubular reactor 100. Adjacent mixing elements 60 are in contact with each other, and in this case are not attached or fused to each other. The mixing elements 60A–F are kept in approximately static relation to the tubular reactor 100 by mixing-element fixing means 104, 106. The fixing means 104, 106 shown comprise a open end cap (S-shaped as illustrated) fixable or fixed across both ends of the tubular reactor 100; these are capable of allowing fluid flow therethrough and are capable of holding and/or compressing the mixing elements 60A–F together within the tubular reactor. Each of the mixing elements e.g. 60C in the tubular reactor 100 are statically arranged so as to be in a rotated orientation (here, by about 90°) about the longitudinal axis of the tubular reactor 100 relative to the mixing element e.g. 60B, 60D on either side of it.

In the arrangement shown in FIG. 10, the first element 60A splits and mixes the stream from side to side, the second element 60B splits and mixes the stream in an up-down direction, the third element 60C splits and mixes the stream side to side, etc. etc. This arrangement ensures good efficient and rapid mixing and splitting of streams in both directions transverse to the axial direction and is suitable for turbulent/ plug flow in the tubular reactor/housing 100 and/or immiscible liquid streams. In general, the "Sulzer® SMV-type" geometry of the mixing elements 60 is selected on considerations regarding versatility. These mixing elements 60 can handle low viscosity solvents but also gas/liquid systems and immiscible liquids of medium viscosity without generating excessive pressure drop.

Example 8

"Kenics KM-Type" Static Mixer and Mixing Elements

Figure 11:
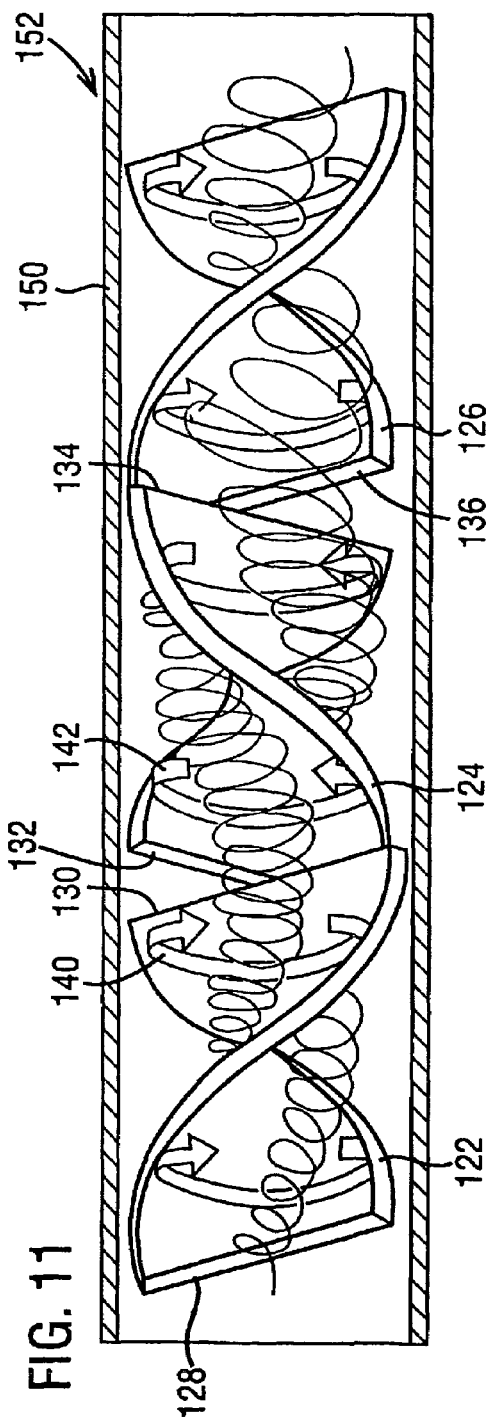
FIG. 11 is a top perspective view of three "Kenics KM-type" static mixing elements axially disposed in a (cut-away) tubular reactor/housing, as described in Example 8, showing the movement and rotation of the fluid flowing along the tubular reactor/housing.
Figure 12:
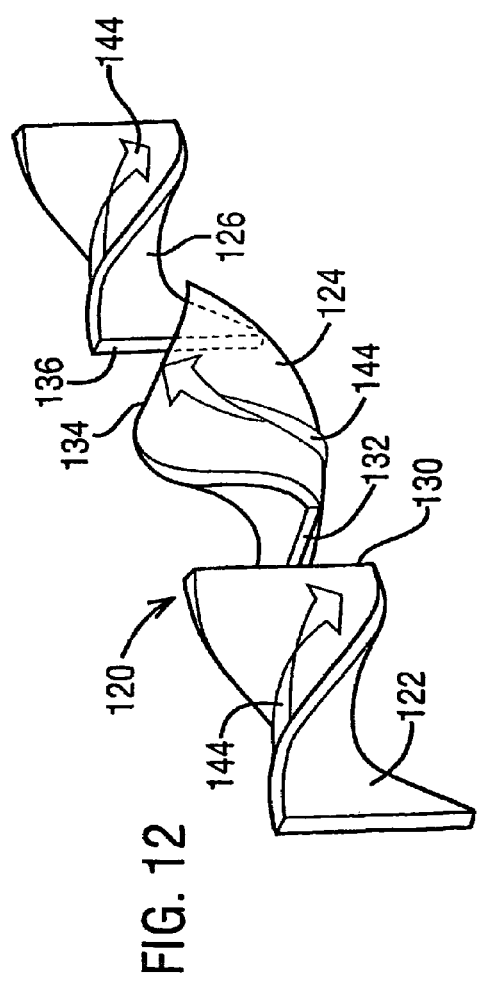
FIG. 12 is a top perspective view of three "Kenics KM-type" static mixing elements as described in Example 8.

FIGS. 11 and 12 are top perspective views of three "Kenics KM-type" static mixing elements axially disposed in a (cut-away) tubular reactor/housing, as described in the general description hereinabove.

With reference to FIGS. 11 and 12, a mixing structure 120 comprises three Kenics® KM static mixing elements 122, 124, 126, of the type obtainable from Chemineer, UK or US (address hereinabove), either fused together or separate but in contact with each other. The mixing elements 122, 124, 126 are plates, formed from SS316-type Fe—Ni—Cr—Mo metal alloy, which are helically-twisted about their longitudinal axis. The elements are aligned in series in the axial direction (FIG. 12) and in use have been inserted axially within and in substantially static relation to a tubular reactor 150 (e.g. length 20 cm, outside diameter 0.5 cm, inside diameter 0.33 cm). The mixing elements 122, 124, 126 in series have a alternating right- and left-handed helically-twisted orientation as shown, i.e. they having alternating rotational directions 140, 142.

31

Each mixing element is a plate with about 180° of helical twist as shown in the FIGS. 11 and 12. A leading edge 130, 134 of each element 122, 124 is located at about 90° to a trailing edge 132, 136 of the following element 124, 126. As the fluids pass through each element, they are divided by the power of two because each successive element is offset by about 90°. The helical twist angle, offset angle, width and height of the mixing element may vary depending on the property of the feed.

As shown in the FIGS. 11 and 12, the helical twist of the mixing elements creates a helical fluid flow path 144 between the inner circumferential walls 150 of the tubular reactor and the plates 122–126, the flow path being split in 2 at each element intersection 130–132, 134–136 and the next helical path is in the opposite angular direction (cf, 140, 142). FIG. 11 shows the movement and rotation 140, 142 of the fluid flowing along the tubular reactor/housing. The figures show that the mixing elements 122–126 improve the degree of fluid mixing by imposing some radial and angular momentum on the fluid.

The total number of mixing elements 122–124 in the tubular reactor 150 can vary with the mixing performance per element, which depends on the size of the element and the flow rate used, but in this case there are 27 elements in series in the tube 150.

Example 9

Vortex Mixer as Stream-mixing Means

Figure 13:
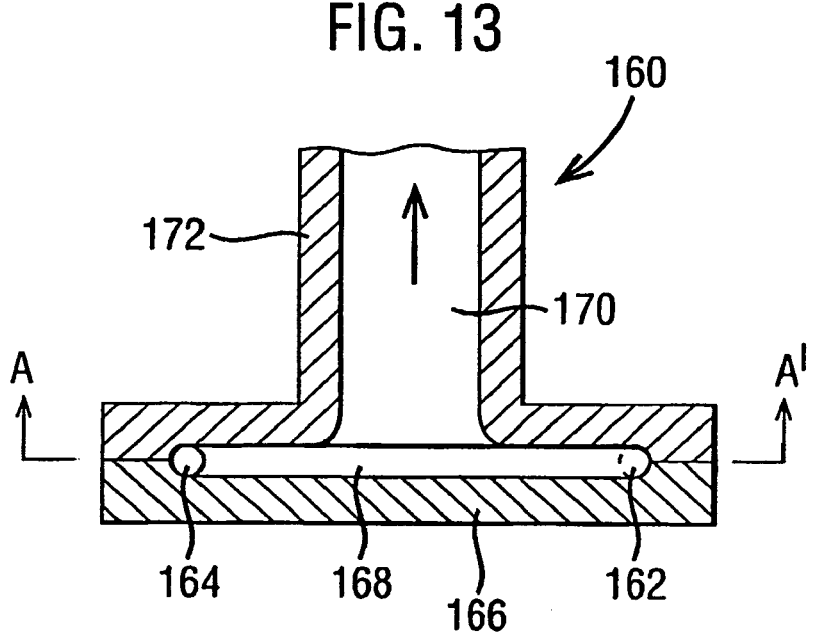
FIG. 13 is a cross-sectional view of a vortex mixer as described in Example 9.
Figure 14:
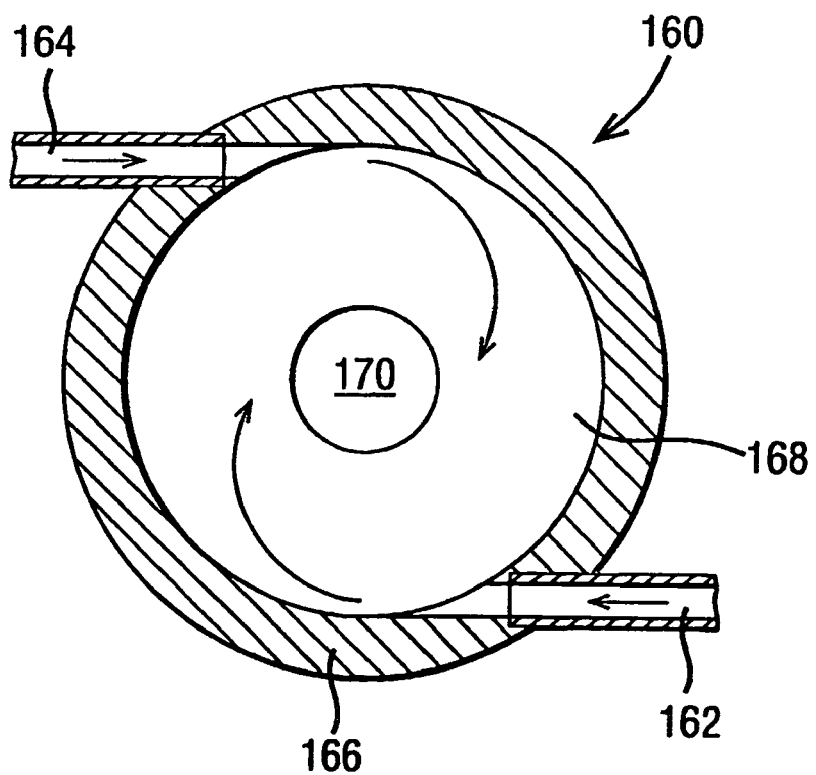
FIG. 14 is a cross-sectional view along line A–A' of the vortex mixer as shown in FIG. 13 and described in Example 9.

FIGS. 13 and 14 illustrate, in cross-sectional views, a vortex mixer which can optionally be used in the processes of Examples 2–5 and/or as part of the apparatus of FIG. 5 (Example 6), in order to give a preliminary mixing of the two reagent streams, firstly the formula (II) compound and Boc$_2$O stream and secondly the aqueous KOH stream, before the combined stream enters the static mixer(s) or plug flow reactor. It is particularly suitable for use as the "mixing chamber" of FIG. 4 and used in Example 5.

With reference to FIGS. 13 and 14, a vortex mixer 160 comprises a metal casing 166, 172 in the form of a hollow disc 166 having an open-ended axially disposed outlet 172. The hollow space in the disc is a disc-shaped (flat-cylindrical) mixing chamber 168. Two reagent inlets 162, 164 leading outside the casing 166 are connected to the circumference of the mixing chamber 168 and are directed tangentially to the circumference. The reagent inlets 162, 164 are in liquid communication with the reagents stored in tanks or other vessels (not shown) and the outlet 170, 172 is connected via a short length of pipe (not shown) with the upstream end of a tubular reactor (not shown).

Possible dimensions of the vortex mixer are disclosed in page 2 lines 31–37 of WO 00/53282. The vortex mixer casing 166, 172 is made of metal; for example stainless steel or a metal alloy containing 1, 2, 3 or more of Fe, Ni, Cr, Mo, e.g. a Fe—Ni—Cr—Mo alloy such as SS316.

In use, the vortex mixer 160 is preferably cooled to about −30 to about 0° C. by submerging in a coolant bath for example containing ice/water or ethylene glycol (e.g. about −15° C.). The reagent streams are pumped into the mixing chamber 168 via inlets 162, 164 and are at least partially mixed therein by generation of a vortex in the mixing chamber 168 and/or in the outlet space 170. The mixed reagents exit out of the outlet 170, 172 and into the tubular reactor.

32

Example 10

Preparation of 4-aminomethyl-3-methoxyimino-pyrrolidinium dimethanesulfonate (AM19) from 1-(N-t-butoxycarbonyl)-4-(N-t-butoxycarbonyl)aminomethylene-pyrrolidin-3-one (AM11)

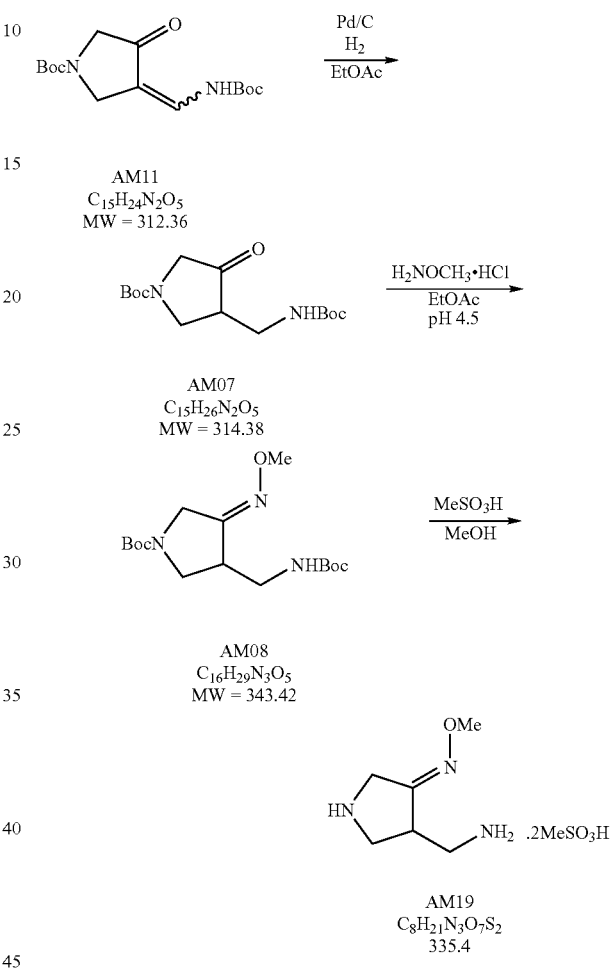

Procedure:

A. Conversion of 1-(N-t-butoxycarbonyl)-4-(N-t-butoxycarbonyl)aminomethylene-pyrrolidin-3-one (AM11) to 1-(N-t-butoxycarbonyl)-4-(N-t-butoxycarbonyl)aminomethyl-pyrrolidin-3-one (AM07) in situ 1) 1-(N-t-butoxycarbonyl)-4-(N-t-butoxycarbonyl)aminomethylene-pyrrolidin-3-one (AM11) (100 g; 0.32 moles) and 10% palladium on charcoal (7.5 g; ex PMC type 3310C [shell/reduced form ca. 56% water]) are suspended in ethyl acetate (400 ml; 4 volumes). The ethyl acetate does not have to be specially dried, but preferably should not be so wet that a two-phase solvent system is created (to avoid potential problems with the catalyst).

2) The mixture is hydrogenated at 25–30° C. under hydrogen at 30 psig for approx. 4 hours. Take samples for hplc every hour.

3) The 10% palladium on charcoal catalyst is removed by filtration via celite and filter bed washed with ethyl acetate (100 ml; 1 volume).

B. Conversion of 1-(N-t-butoxycarbonyl)-4-(N-t-butoxycarbonyl)aminomethyl-pyrrolidin-3-one (AM07), formed in situ, to 1-(N-t-butoxycarbonyl)-4-(N-t-butoxycarbonyl)aminomethyl-pyrrolidin-3-one O-methyloxime (AM08) in situ 4) The solution of 1-(N-t-butoxycarbonyl)-4-(N-t-butoxycarbonyl)aminomethyl-pyrrolidin-3-one (AM07) in ethyl acetate (5 volumes), which is the combined filtrate of step 3) above, is treated with a solution of methoxylamine hydrochloride in water (95 ml; 107 g; 0.39 moles @ 34.4% w/v).

5) Adjust the pH to 4.5 with 40% aqueous sodium hydroxide solution (approx. 50 ml used) and heat to reflux (ca. 73° C.) for approx. 1–2 hr. The end of the reaction will be determined by hplc.

6) After cooling to ca. 50° C. the phases are allowed to separate and the lower aqueous phase run off and discarded.

7) Wash with water (2×100 ml).

8) Evaporate to approx. 150 ml under vacuum to azeotrope out water. Determine water content of concentrate by Karl Fisher (KF) method (require <0.1% $H_2O$). Repeat azeotrope with ethyl acetate (200 ml) if necessary (i.e. if not at required low-water level), again evaporating to approx. 150 ml under vacuum.

9) Add methanol (ca. 300 ml). Re-evaporate to remove azeotropically most of the remaining ethyl acetate, to form approx 150 ml of solution. Add further methanol (300 ml) to make the solution of in situ AM08 up to a total volume to 450 ml. The solution should contain ≦5%, preferably ≦1%, more preferably ≦0.2% of ethyl acetate by volume of pure solvent or by volume of solution. Take sample for water analysis by Karl Fisher method.

C. Conversion of 1-(N-t-butoxycarbonyl)-4-(N-t-butoxycarbonyl)aminomethyl-pyrrolidin-3-one O-methyloxime (AM08), present in situ, to 4-aminomethyl-3-methoxyimino-pyrrolidinium dimethanesulfonate (AM19)

10) The dried solution of 1-(N-t-butoxycarbonyl)-4-(N-t-butoxy-carbonyl)aminomethyl-pyrrolidin-3-one O-methyloxime (AM08) in methanol, produced in step 9) above, is cooled to 20° C.

11) Methanesulphonic acid (52 ml; 77 g; 2.5 equiv) is added over 15 mins keeping the temperature below 25° C. The solution is heated to 40° C. over 30 minutes and then seeded with AM19 unless crystallisation has already occurred. The reaction mixture is maintained at 40–45° C. for approx 4–5 hrs. Take samples as required for ipc.

12) Cool to 20–25° C. and stir for 1 hour then isolate the crude product by filtration under nitrogen and wash with further methanol (200 ml).

13) The wet crude product is removed from the filter and weighed. Expected 'wet' yield is approx. 100–110 g.

14) Crude AM19 is suspended in methanol (4 volumes; approx. 360 ml*) and heated to reflux for 1 hour.

15) After cooling to 20° C., stir for 1 hour. Filter AM19 and wash with methanol (2 volumes; approx. 180 ml*)

*exact quantity will be determined based on methanol content of 'wet' product.

16) Dry solid AM19 at 40° C. under vacuum.

17) Expected yield of AM19 (4-aminomethyl-3-methoxyimino-pyrrolidinium dimethanesulfonate=4-(aminomethyl)pyrrolidin-3-one-O-methyloxime dimethanesulphonic acid salt) is approx. 74–75 g (69–70% from AM11).

Example 11

=Example 3 of WO 01/17961 A2

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid Triethylamine (5.1 ml) was added to 7-chloro-1-cyclopropyl-6-fluoro-4-oxo-1,4-dihydro-1,8-naphthyridine-3-carboxylic acid (3.05 g) in water (25 ml) at 15–20° C. and the mixture stirred for 20 min. 4-Aminomethyl-3-methoxyimino-pyrrolidinium dimethanesulfonate ("AM19", 3.86 g) was added, followed by water (5 ml), and the mixture stirred at 20–25° C. for 17% hours. The resulting product was filtered and the cake washed with water (30 ml) followed by ethanol (30 ml) and dried under vacuum at 50° C. to give the title compound as a white solid (4.23 g). (102% as is, 86% on assay). Characterising data were consistent with a standard sample of the title compound.

Example 12

=Example 4 of WO 01/17961 A2

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate A solution of methanesulfonic acid (0.33 g, 3.43 mmol) in dichloromethane (1 ml) was added to a suspension of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid (1.5 g at 89.9% purity, 3.46 mmol) in a mixture of dichloromethane (23.2 ml) and ethanol (2.7 ml) at 30° C. The mixture was stirred at 30° C. for 3 hours then cooled to 20° C. and filtered. The cake was washed with dichloromethane (20 ml) and dried at 50° C. under vacuum to give the title compound (1.71 g) (102% as is, 91% on assay). Characterising data were consistent with a standard sample of the title compound.

Example 13

=Example 5 of WO 01/17961 A2

Synthesis of (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate sesquihydrate (the "methanesulfonate sesquihydrate")

(R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate (27.5 g at 91% purity, 51.4 mmol) was stirred in a mixture of isopropanol (150 ml) and water (75 ml) and heated until a clear solution was obtained (52° C.). The solution was cooled to 34° C. and seed crystals of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate added. The resulting suspension was allowed to cool to 25° C. over 1 hour and stirred for 18 hours. The slurry was cooled to 0–4° C., stirred for 2 hours, then filtered and the cake washed with isopropanol (30 ml). The product was sucked dry for 2 hours and then further dried at 50° C. under vacuum. The dried product was exposed to the atmosphere, preferably under humid conditions, to give the methanesulfonate sesquihydrate, 22.9 g (92%). Characterising data were consistent with a standard sample of the title compound.

Example 14

Gemifloxacin Methanesulfonate Sesquihydrate—Large Scale Version of Example 13

This large-scale process was performed substantially as in Example 13 having scaled up the reagents and solvents (e.g. using about 100 kg, or more or less, of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate). However, instead of exposing the dried product to the atmosphere, the dried product was exposed to a passing stream of humid (wet) nitrogen, for example having about 70% to about 95% relative humidity, at ambient temperature (e.g. 20–25° C.), either overnight (e.g. about 18 hours) or for some other necessary period, to give the methanesulfonate sesquihydrate. The wet nitrogen was obtained by bubbling dry nitrogen through a water bubbler.

Example 15

(=Example 1 of WO 00/17199 A1): Preparation of Gemifloxacin Methanesulfonate Sesquihydrate From Gemifloxacin "Free Base" Using Direct Salt and Hydrate Formation Process According to WO 00/17199 A1

To a suspension of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid (20.00 g, 51.4 mmol) in isopropanol (120 ml) and water (60 ml) was added methanesulfonic acid (3.300 ml, 50.9 mmol) at 38–40° C. The resultant dark brown solution was stirred for 15 min after which time charcoal (6.00 g of Darco G-60) was added. The suspension was stirred at 38–40° C. for 4 h then filtered. The filtrate was allows to cool to 30° C. and seed crystals of (R,S)-7-(3-aminomethyl-4-syn-methoxyiminopyrrolidin-1-yl)-1-cyclopropyl-6-fluoro-4-oxo-1,4-dihydro-1,8-naphthyridine-3-carboxylic acid methanesulfonate sesquihydrate (15 mg) added. A precipitate began to form within 15 min. The suspension was allowed to cool to 20–23° C. over 90 min and was stirred for 36 h. The slurry was cooled to 0–5° C. for 60 min then filtered and washed with isopropanol (50 ml and 44 ml). The product was sucked dry for 30 min and then further dried at 50–55° C. under vacuum. The dried product was exposed to the atmosphere for about 18 hours, preferably under humid conditions, or alternatively under humid nitrogen as in Example 14, to give the methanesulfonate sesquihydrate 21.29 g (85%), purity >99.5% by HPLC.

Figure 15:
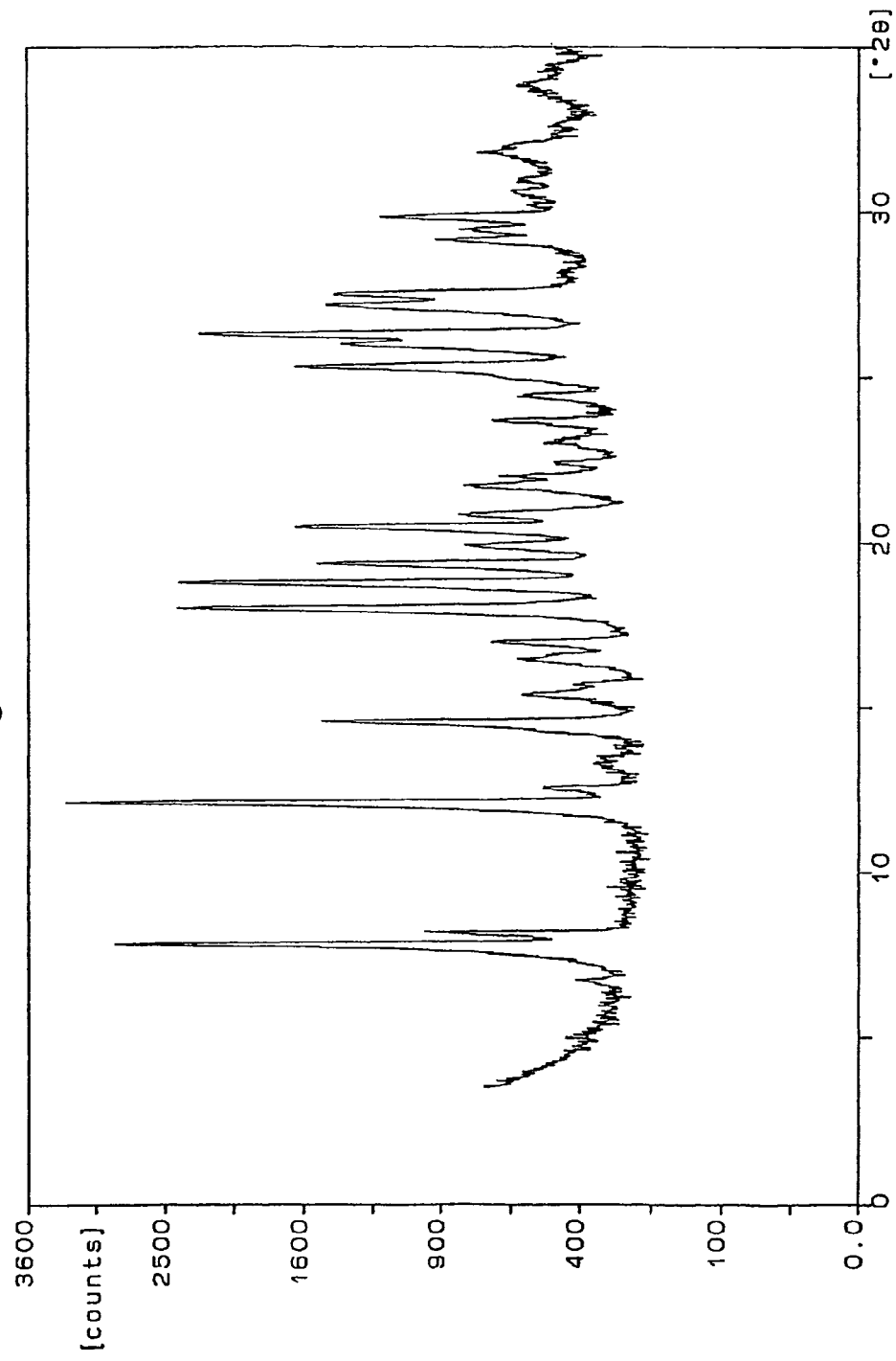
FIG. 15 is an X-ray diffraction pattern of gemifloxacin methanesulfonate sesquihydrate as described in Example 15. The compound shows characteristic peaks at approximately 2θ=8.2, 12.2 and 14.6°.

The X-ray diffraction pattern of the gemifloxacin methanesulfonate sesquihydrate was measured as follows:

The X-ray diffraction pattern of gemifloxacin methanesulfonate sesquihydrate is shown in FIG. 15. The compound shows characteristic peaks at approximately $2\theta=8.2$, 12.2 and 14.6°.

The invention claimed is:

1. A process for the production of a compound of formula (I):

wherein $P_1$ and $P_2$, which may be the same or different, are amino protecting groups, which comprises protection of a compound of formula (II):

in solution phase continuous operation mode,
wherein said process is conducted in reaction equipment adapted for use in continuous processing mode and in which mixing is induced passively through the fluid flow;
wherein said reaction equipment comprises a plug flow reactor.

2. A process as claimed in claim 1 wherein protection of the compound of formula (I) is performed by reacting the compound of formula (I) with a reagent for introducing the amino-protecting group $P_2$, in the presence of a base.

3. A process as claimed in claim 2 wherein the reagent for introducing the amino-protecting group is t-butoxycarbonyl anhydride.

4. A process as claimed in claim 2, wherein the reagent for introducing the amino-protecting group is an isopropanol/water solution.

5. A process as claimed in claim 1, wherein $P_1$ and $P_2$ are amino protecting groups removable by acidic conditions.

6. A process as claimed in claim 1, wherein the protecting group $P_1$ and/or the protecting group $P_2$ is formyl, acetyl, trifluoroacetyl, benzoyl, para-toluenesulfonyl, methoxycarbonyl, ethoxycarbonyl, t-butoxycarbonyl, benzyloxycarbonyl, para-methylbenzyloxycarbonyl, trichioroethoxycarbonyl, beta-iodoethoxycarbonyl, benzyl, para-methoxybenzyl, trityl, tetrahydropyranyl or pivaloyl.

| | | | |
|---|---|---|---|
| Diffractometer type: | PW1710 BASED | Monochromator used: | YES |
| Tube anode: | Cu | Start angle [°2θ]: | 3.500 |
| Generator tension [kV]: | 40 | End angle [°2θ]: | 35.000 |
| Generator current [mA]: | 30 | Step size [°2θ]: | 0.020 |
| Wavelength Alpha1 [Å]: | 1.54060 | Maximum intensity: | 2970.250 |
| Wavelength Alpha2 [Å]: | 1.54439 | Time per step [s]: | 2.300 |
| Intensity ratio (alpha1/alpha2): | 0.500 | Type of scan: | STEP |
| Divergence slit: | AUTOMATIC | Minimum peak tip width: | 0.10 |
| Irradiated length [mm]: | 12 | Maximum peak tip width: | 1.00 |
| Receiving slit: | 0.1 | Peak base width: | 2.00 |
| Spinner: | ON | Minimum significance: | 0.50 |

7. A process as claimed in claim 1 wherein $P_1$ and $P_2$ are both t-butyloxycarbonyl.

8. A process as claimed in claim 2 wherein the base is aqueous potassium hydroxide solution.

9. A process as claimed in claim 8 wherein the base is 30% w/w to 50% aqueous potassium hydroxide solution.

10. A process as claimed in claim 1 which is carried out using isopropanol/water as solvent.

11. A process as claimed in claim 2, wherein in the continuous operation mode, a stream of aqueous base and a stream of a solution of the 1-(N-protected)-4-aminomethylene-pyrrolidin-3-one of formula (II) containing the reagent for introducing the amino-protecting group are brought together prior to quenching in acid.

12. A process as claimed in claim 1, which is conducted at a temperature of less than 20° C.

13. A process according to claim 1 wherein the process is conducted in reaction equipment adapted for use in continuous processing mode and comprising a substantially tubular reactor to form the product of formula (I) and in which or upstream of which two or more streams of the reagents/starting materials are brought together.

14. A process according to claim 1 wherein the process is conducted in reaction equipment adapted for use in continuous processing mode, and wherein the mixing time in the reaction equipment is shorter than the reaction half life (the time required to reach 50% conversion).

15. A process according to claim 1 wherein the process is conducted in reaction equipment adapted for use in continuous processing mode and being a non back-mixed system.

16. A process according to claim 1 wherein the plug flow reactor comprises a jacketed tubular reactor fitted inside with internal mixing elements which continually split and remix the reaction streams promoting mass and heat transfer, whereby a uniform plug flow profile with turbulent fluid flow is achieved.

17. A process as claimed in claim 1 wherein the reaction equipment comprises one or more static mixers.

18. A process as claimed in claim 1 wherein one or more of the static mixers or the plug flow reactor comprises one or more static mixing elements, wherein some, most or all of the mixing elements are adapted to split and mix a fluid stream flowing therethrough substantially in one dimension transverse to the fluid flow.

19. A process as claimed in claim 1 wherein one or more of the static mixers or the plug flow reactor comprises one or more static mixing elements, wherein some, most or all of the mixing elements comprise a plurality of stacked corrugated sheets, wherein the grooves of each corrugated sheet are transverse to the grooves of any directly adjacent corrugated sheet.

20. A process as claimed in claim 19, wherein a plurality of the mixing elements are substantially axially aligned within a or the substantially tubular reactor, with the corrugated sheets arranged so as to allow fluid flow longitudinally along the tubular reactor.

21. A process as claimed in claim 20, wherein some or all of the mixer elements in the tubular reactor are statically arranged so as to be in a rotated orientation about the longitudinal axis relative to one or both of the neighbouring mixing elements.

22. A process as claimed in claim 17, wherein one or more of the static mixers comprise one or more mixing elements arranged substantially axially within and in substantially static relation to a substantially tubular reactor, and wherein the mixing elements define at least one substantially helical fluid flow path in the axial direction between the mixing element and the inner circumferential walls of the tubular reactor.

23. A process as claimed in claim 22 wherein two substantially helical fluid flow paths are defined by the mixing elements.

24. A process as claimed in claim 22 wherein the mixing elements are helically-twisted about their axis so as to define the at least one substantially helical fluid flow path.

25. A process as claimed in claim 24, wherein one or more (e.g. all) of the static mixers comprise a series of alternating right- and left-handed helically-twisted mixing elements, i.e. having alternating rotational directions.

26. A process as claimed in any of claims 22, wherein each or most mixing element(s) is/are a plate and a leading edge of each element is located substantially perpendicularly to a trailing edge of the following element.

27. A process as claimed in claim 1, wherein the residence time is about 5 to about 60 seconds.

28. A process as claimed in claim 27, wherein the residence time is 10 to 30 seconds.

29. A process as claimed in claim 22 wherein protection of the compound of formula (I) is performed by reacting the compound of formula (I) with a reagent for introducing the amino-protecting group $P_2$, in the presence of a base and wherein the base is used at a stoichiometry of $^3 6$ equivalents relative to the compound of formula (II).

30. A process as claimed in claim 22 wherein protection of the compound of formula (I) is performed by reacting the compound of formula (I) with a reagent for introducing the amino-protecting group $P_2$, in the presence of a base and wherein the base is used at a stoichiometry of 5 to 12 equivalents relative to the compound of formula (II).

31. A process as claimed in claim 1 wherein two, three or more streams of the reagents/starting materials are brought together upstream of a or the reactor (a) by a direct junction which contains substantially no mixing chamber at the junction, or (b) by a stream-mixing means comprising a substantial mixing chamber having two, three or more reagent inlets in fluid communication with the stored reagents and an outlet in fluid communication with the reactor.

32. A process as claimed in claim 31 wherein the stream-mixing means comprises a substantial mixing chamber and is a vortex mixer adapted to mix at least partly the reagent streams in use by generation of a vortex in the mixing chamber and/or in the outlet.

33. A process as claimed in claim 31 wherein the stream-mixing means is at a temperature of about 0° C. to about −15° C., preferably about −5° C. to about −15° C.

34. A process for the production of a compound of formula (III), or a pharmaceutically acceptable salt and/or hydrate thereof:

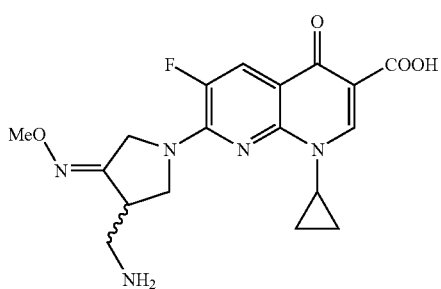

(III)

which comprises:
producing a compound of formula (I) according to a process as claimed in claim 1; and
converting a compound of formula (I) to a compound of formula (IV):

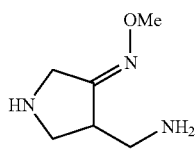

(IV)

or a salt thereof, followed by reaction of the compound of formula (IV) or a salt thereof, with a compound of formula (V):

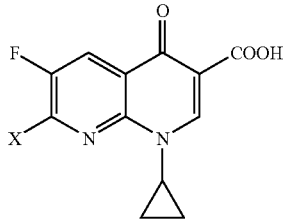

(V)

wherein X is a leaving group; and
optionally forming a pharmaceutically acceptable salt and/or hydrate thereof.

35. A process as claimed in claim 34 wherein the reaction of the compound of formula (IV) and the compound of formula (V) is conducted in a solvent in the presence of a base.

36. A process as claimed in claim 34 wherein the compound of formula (III) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or a hydrate thereof.

37. A process as claimed in claim 36 wherein the compound of formula (III) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate sesquihydrate.

38. A process for the production of a compound of formula (III), or a pharmaceutically acceptable salt and/or hydrate thereof:

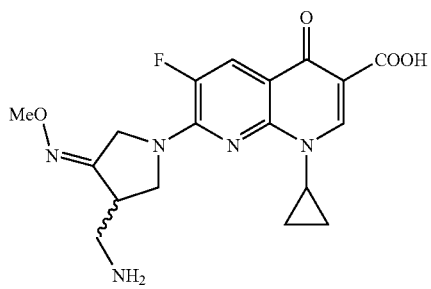

(III)

which comprises:
(1) producing a compound of formula (I) as defined according to a process of claim 1; and
(2) converting a compound of formula (I) as defined in claim 1, to a compound of formula (IV):
or a salt thereof,

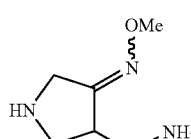

(IV)

followed by
(3) reaction of the compound of formula (IV) or the salt thereof, with a compound of formula (V)

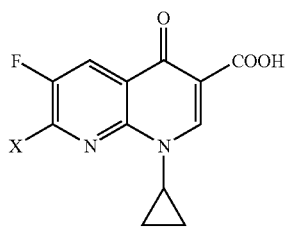

(V)

wherein X is a leaving group; and
(4) optionally forming a pharmaceutically acceptable salt and/or hydrate thereof.

* * * * *